(12) United States Patent
Dufrane et al.

(10) Patent No.: US 8,168,215 B2
(45) Date of Patent: May 1, 2012

(54) ALGINATE COATED, COLLAGEN MATRIX CELLULAR DEVICE, PREPARATIVE METHODS, AND USES THEREOF

(75) Inventors: Denis Dufrane, Wavre (BE); Pierre Rene Raymond Gianello, Rixensart (BE); Jan Egil Melvik, Oslo (NO)

(73) Assignee: FMC Biopolymer AS

( * ) Notice: Subject to any disclaimer, the term of this patent is extended or adjusted under 35 U.S.C. 154(b) by 1117 days.

(21) Appl. No.: 11/762,680

(22) Filed: Jun. 13, 2007

(65) Prior Publication Data

US 2008/0050417 A1 Feb. 28, 2008

Related U.S. Application Data

(60) Provisional application No. 60/814,404, filed on Jun. 16, 2006.

(51) Int. Cl.
*A61F 13/00* (2006.01)
*C12N 5/00* (2006.01)

(52) U.S. Cl. ........ 424/443; 424/93.1; 424/484; 435/325

(58) Field of Classification Search .................. 424/400, 424/422, 484, 443, 93.1; 435/325
See application file for complete search history.

(56) References Cited

U.S. PATENT DOCUMENTS

| | | | |
|---|---|---|---|
| 2,036,934 A | 4/1936 | Green et al. | |
| 2,128,551 A | 8/1938 | Emile et al. | |
| 2,426,125 A | 8/1947 | Steiner et al. | |
| 3,772,266 A | 11/1973 | Pettitt et al. | |
| 3,948,881 A | 4/1976 | Strong | |
| 5,429,821 A | 7/1995 | Dorian et al. | |
| 5,738,876 A | 4/1998 | Enevold | |
| 5,855,613 A | 1/1999 | Antanavich et al. | |
| 6,020,200 A | 2/2000 | Enevold | |
| 6,165,225 A | 12/2000 | Antanavich et al. | |
| 6,171,610 B1 | 1/2001 | Vacanti et al. | |
| 6,334,968 B1 | 1/2002 | Shapiro et al. | |
| 6,372,244 B1 | 4/2002 | Antanavich et al. | |
| 6,419,920 B1 * | 7/2002 | Mineau-Hanschke | 424/93.21 |
| 6,642,363 B1 | 11/2003 | Mooney et al. | |
| 6,699,470 B1 | 3/2004 | Ameer et al. | |
| 7,790,193 B2 * | 9/2010 | Melvik et al. | 424/423 |
| 7,790,699 B2 * | 9/2010 | Melvik et al. | 514/54 |
| 2002/0094569 A1 | 7/2002 | Yu et al. | |
| 2004/0101518 A1 | 5/2004 | Vacanti et al. | |

FOREIGN PATENT DOCUMENTS

| | | |
|---|---|---|
| WO | 9519430 | 7/1995 |
| WO | 9519743 | 7/1995 |
| WO | 9628029 | 9/1996 |
| WO | 0049135 | 8/2000 |
| WO | 9324077 | 7/2007 |

OTHER PUBLICATIONS

King, Scott R. et al., Requirements for Encapsulation Technology and the Challenges for Transplantation of Islets of Langerhans, Graft, 2001, pp. 491-499, vol. 4, Issue 7.

Dufrane, Denis et al., The influence of implantation site on the biocompatibility and survival of alginate encapsulated pig islets in rats, Biomaterials, 2006, pp. 3201-3208, 27.

Dufrane, D. et al., Is the Expression of Gal-alpha1, 3Gal on Porcine Pancreatic Islets Modified by Isolation Procedure?, Transplantation Proceedings, 2007, pp. 455-457, 37.

Dufrane, Denis et al., Streptozotocin-Incuded Diabetes in Large Animals (Pigs/Primates): Role of GLUT@ Transporter and Beta-cell Plasticity, Cell therapy and Islet Transplantation, 2006, pp. 36-45, 81.

Dufrane, Denis et al., Clinical application of a physically and chemically processed human substitute for dura mater, J. Neurosurg., 2003, pp. 1198-1202, vol. 98.

Dufrane, D. et al., Physical and chemical processing for a human dura mater substitute, Biomaterials, 2002, pp. 2979-2988, 23.

Dufrane, Denis, et al., Six-Month Survival of Microencapsulated Pig Islets and Alginate Biocompatibility in Primates: Proof of Concept, Transplantation, May 15, 2006, pp. 1-8, vol. 81, No. 9.

Dufrane, Denis, Encapsulation of Pig Islets by Alginate Matrix to Correct Streptozotocin-Induced Diabetes in Primates Without Immunosuppression, Universite catholique de Louvain, Faculty of Medicine, Laboratory of Experimental Surgery, Jun. 2006, pp. 1-158.

Genes, Nicholas G. et al., Effect of substrate mechanics on chondrocyte adhesion to modified alginate surfaces, Archives of biochemistry and Biophysics, 2004, pp. 161-167, 422.

Markusen, Julia F. et al., Behavior of Adult Human Mesenchymal Stem Cells Entrapped in Alginate-GRGDY Beads, Tissue Engineering, 2006, pp. 821-830. vol. 12, No. 4.

Rowley, Jon A. et al., Alginate hydrogels as synthetic extracellular matrix materials, Biomaterials, 1999, pp. 45-53, 20.

Marler, Jennifer J. et al., Soft-Tissue Augmentation with Injectable Alginate and Syngeneic Fibroblasts, Plastic and Reconstructive Surgery, 2000, pp. 2049-2058.

Connelly, John T. et al., Inhibition of in vitro chondrogenesis in RGD-modified three-dimensional alginate gels, Biomaterials, 2007, pp. 1071-1083, 28.

Comisar, Wendy A. et al., Multi-scale modeling to predict ligand presentation within RGD nanopatterned hydrogels, Biomaterials 2006, pp. 2322-2329, 27.

Alsberg, Eben et al., Engineering growing tissues, PNAS, Sep. 17, 2002, pp. 12025-12030, vol. 99, No. 19.

Rowley, Jon A. et al., Alginate type and RGD density control myoblast phenotype, 2001, pp. 217-223.

Dufrane, D. et al, Impact of Porcine Islet Size on Cellular Structure and Engraftment After Transplantation, Pancreas, Mar. 2005, pp. 138-147, vol. 30, No. 2.

Dufrane, D. et al., Parameters favouring successful adult pig islet isolations for xenotransplantation in pig-to-primate models, Xenotransplantation, 2006, pp. 1-11, 13.

August, Alexander D. et al, Alginate Hydrogels as Biomaterials, Macromol. Biosci., 2006, pp. 623-633, 6.

(Continued)

*Primary Examiner* — Ruth Davis
(74) *Attorney, Agent, or Firm* — FMC Corporation

(57) ABSTRACT

The present invention is directed to cellular devices comprising a collagen matrix, cell layer, and gelled alginate layer, processes for producing the devices, methods of implanting the devices, and methods of treatment thereof.

36 Claims, 21 Drawing Sheets

OTHER PUBLICATIONS

Ma, Hsiao-Li et al., Chondrogenesis of human mesenchymal stem cells encapsulated in alginate beads, 2002, pp. 273-281, Wiley Periodicals, Inc.

Grimmer, J. Fredrik et al., Tracheal Reconstruction Using Tissue-Engineered Cartilage, Arch Otolaryngol Head Neck Surg., Oct. 2004, pp. 1191-1196, vol. 130.

Kreeger, Pamela K. et al., The in vitro regulation of ovarian follicle development using alginate-extracellular matrix gels, Biomaterials, 2006, pp. 714-723, 27.

Loebeack, Anna et al., In vivo characterization of a porous hydrogel material for use as a tissue bulking agent, 2001, pp. 575-581, John Wiley & Sons, Inc.

Dufrane, Denis et al., A simple method using a polymethylpenten chamber for isolation of human pancreatic islets, Pancreas, Apr. 2005, pp. e51-e59, vol. 30, No. 3.

Wang, R. N. et al., Maintenance of beta-cell function and survival following islet isolation requires re-establishment of the islet-matrix relationship, Journal of Endocrinology, 1999, pp. 181-190, 163.

Hinton, Richard et al., A biomechanical analysis of solvent-dehydrated and freeze-dried human fascia lata allografts, The American Journal of Sports Medicine, 1992, pp. 607-612, vol. 20, No. 5.

Dulong, Jean-Luc et al., A Theoretical Study of Oxygen Transfer Including Cell Necrosis for the Design of a Bioartificial Pancreas, Biotechnology and Bioengineering, Apr. 1, 2007, pp. 990-998, vol. 96, No. 5.

Storrs, Richard et al., Preclinical Development of the Islet Sheet, Annals New York Academy of Sciences, pp. 252-266.

Pinkse, Gabrielle G.M. et al., Integrin Signaling via RGD Peptides and Anti-betta 1 Antibodies Confers Resistance to Apoptosis in Islets of Langerhans, Diabetes, Feb. 2006, pp. 312-317, vol. 55.

* cited by examiner

Fig. 15

|      | -4  | 0   | 8    | 12  | 16  | 20  | 24  | 30   | 34   | 42  | 48  | 54 |
|------|-----|-----|------|-----|-----|-----|-----|------|------|-----|-----|----|
| Ctrl+ | 5.4 | >13 | >13  | >13 |     |     |     |      |      |     |     |    |
| Sham | 4.8 | >13 | >13  | >13 |     |     |     |      |      |     |     |    |
| #1   | 5.8 | >13 |      |     |     |     |     |      |      |     |     |    |
| #2   | 5.8 | >13 |      |     |     |     |     |      |      |     |     |    |
| #3   | 5.6 | >13 |      |     |     |     |     |      |      |     |     |    |
| #4   | 5.4 | >13 |      |     |     |     |     |      |      |     |     |    |
| #5   | 6.1 | >13 | 12.8 | 9.4 | 6.4 | 6.6 | 8.2 | 10.4 | >13  | 9.6 | 11.3 | >13 |
| #6   | 4.3 | >13 | 9.6  | 8.2 | 8.3 | >13 | >13 |      |      |     |     |    |
| #7   | 6.5 | >13 | 10.8 | 9.5 | 9.8 | 10.4 | 12.5 |    |      |     |     |    |
| #8   | 7.2 | >13 | 10.3 | 8.3 | 7.5 | 6.7 | 7.2 | 10.4 | 12.9 | 7.4 | 8.5 | in course |

(A)

(B)

ALGINATE COATED, COLLAGEN MATRIX CELLULAR DEVICE, PREPARATIVE METHODS, AND USES THEREOF

This application claims the benefit of priority of U.S. Provisional Application 60/814,404, filed Jun. 16, 2006, which is hereby incorporated by reference in its entirety.

FIELD OF THE INVENTION

The present invention is directed to cellular devices comprising a collagen matrix, cell layer, and gelled alginate layer, processes for producing the devices, methods of implanting the devices, and methods of treatment thereof.

BACKGROUND OF THE INVENTION

For many diseases, cell therapy—implanting living cells within the body—could be a simple, low risk, and cost-effective alternative to whole organ replacement. These types of therapies could also allow efficient use of donor organs, which are in critically short supply. Further, while use of human tissues can clearly prevent problems with rejection of the cells, there is an interest in developing cellular devices that could also utilize cells from other animals such as pigs.

One area of interest is the implantation of pancreatic islets into patients suffering from Type I diabetes in order to produce insulin. A properly designed device could allow for close control over the release of insulin, thereby allowing good regulation of blood glucose levels.

Cell therapy using autologous (self) or mismatched (allogeneic, xenogeneic) cells is likely to succeed clinically only if cells survive at the transplantation site and are protected against immune rejection. Many cell transplantation techniques have been introduced over the years to achieve these objectives, only to be discarded after more careful evaluation and data analysis.

With regard to rejection, encapsulation has been shown to allow transplantation of cells without immunosuppression. In this technique, cells are surrounded by a semipermeable membrane that allows free exchange of oxygen, nutrients, and metabolites while preventing the passage of cells and high molecular weight substances such as immunocytes, antibodies, and complement factors.

However, several limitations exist in implementing such therapy. For example, cell survival depends on nutrient and oxygen availability at the transplantation site. The latter may require neovascularization at the implantation site, a process that requires a significant amount of time. Further, cellular devices may exhibit breakage after several weeks of transplantation and/or an immunosuppressive response, thereby limiting longer term viability and/or retrieval of the devices.

In addition, use of cells from non-human donors presents additional challenges. Porcine tissues and cells are known to be infected with endogenous retroviruses. The genomes of all domesticated swine species tested thus far contain multiple integrated copies of an endogenous C-type retrovirus termed porcine endogenous retrovirus (PERV). Transmission of xenogeneic retroviral infections to xenograft recipients is of particular concern because retroviruses are known to result in lifelong persistent infections. Development of improved cellular devices is, therefore, of interest, which might then reduce or eliminate the risk of PERV contamination and allow the use of cellular material from pigs for various therapeutic uses.

Accordingly, there is an existing need to develop new cellular devices for use in implanting various types of cells without these associated risks and disadvantages. This invention addresses these needs and others.

BRIEF DESCRIPTION OF THE FIGURES

FIGS. 15D and 15E show the device after explantation with vWF staining (D) and toluidine blue staining (E). FIG. 15F shows the incision where a new MCD (FIG. 15E) was implanted subcutaneously.

FIG. 15 depicts glycosylated haemoglobin courses of STZ-induced diabetic cynomolgus prior to diabetes induction (mean of four weeks prior to transplantation), just prior to transplantation (week 0) and every four weeks after eight weeks post transplantation.

SUMMARY OF THE INVENTION

Figure 1:
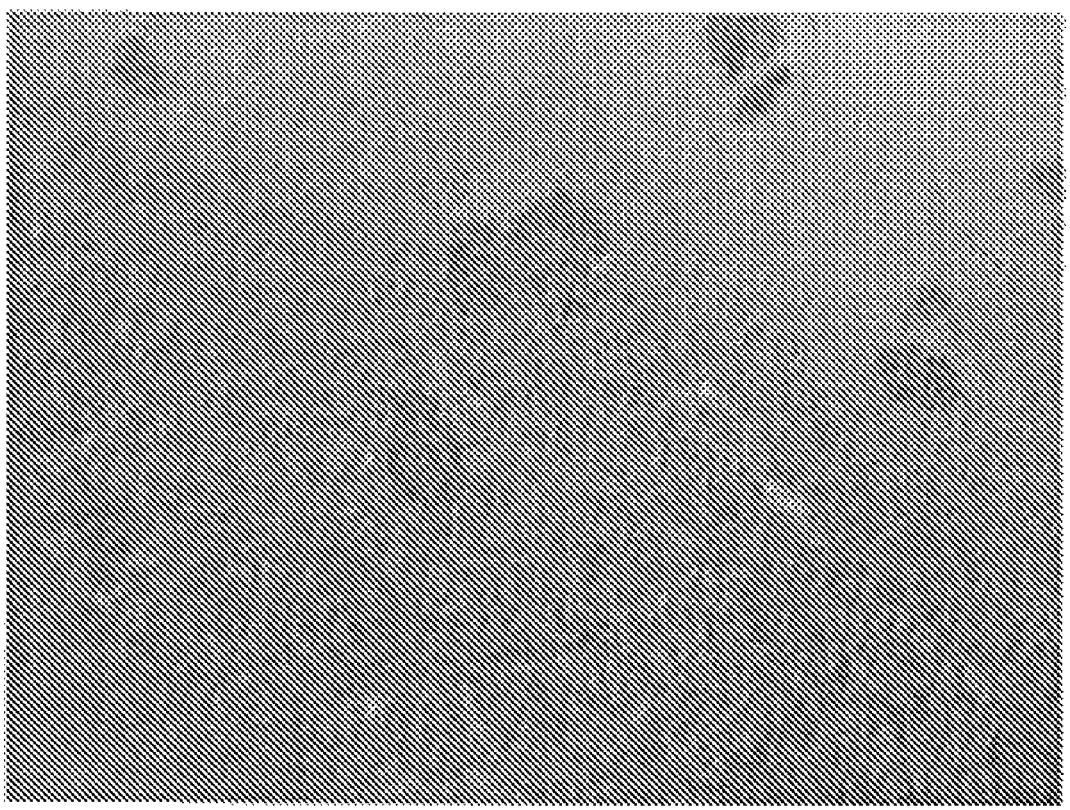
FIG. 1 depicts alginate-microencapsulated pig islets stained by dithyzone.
Figure 2:
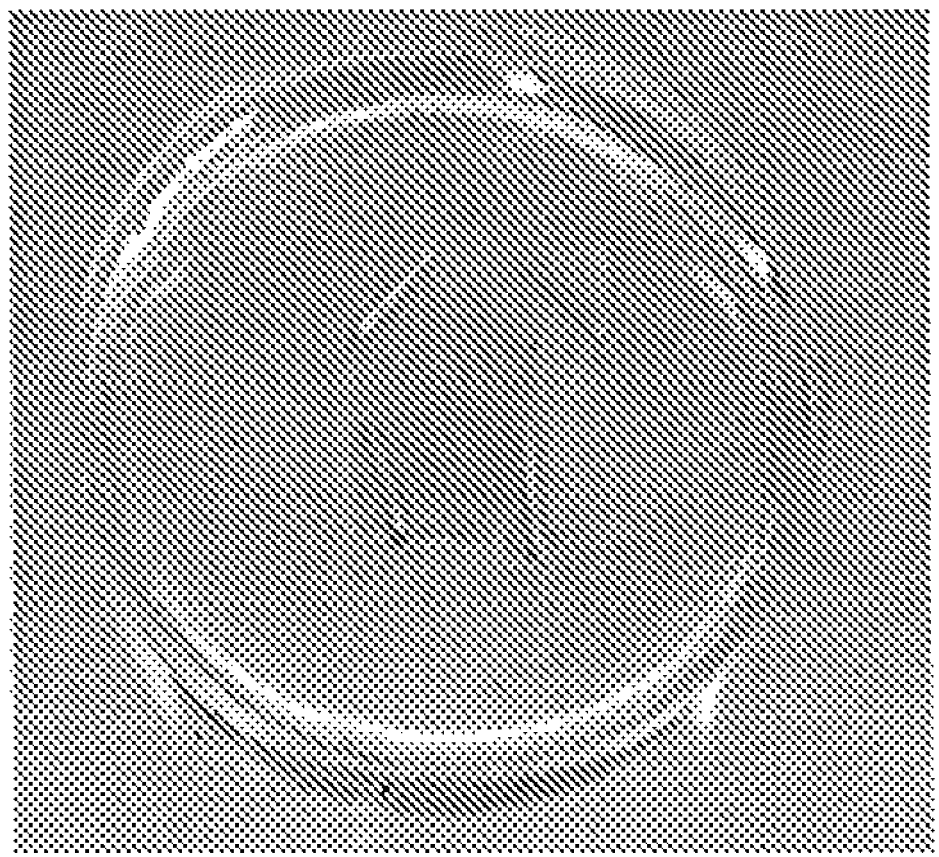
FIG. 2 depicts the cellular devices containing pig islets.

In one aspect, the present invention provides a cellular device comprising:
(a) a collagen matrix having a first side and a second side;
(b) a first cell layer absorbed onto the first side of the collagen matrix; and
(c) a first gelled alginate layer and a second gelled alginate layer; wherein the first gelled alginate layer completely covers the first side of the collagen matrix and the first cell layer; and wherein the second gelled alginate layer completely covers the second side of the collagen matrix.

The present invention further provides a process for forming a cellular device of the invention, comprising:
forming the first cell layer on the first side of the collagen matrix;
forming the first gelled alginate layer so as to completely cover the first side of the collagen matrix and the first cell layer; and
forming a second gelled alginate layer so as to completely cover the second side of the collagen matrix.

The present invention further provides a process for forming a cellular device of the invention, comprising:
forming the first cell layer on the first side of the collagen matrix;
placing the structural support on the first cell layer;
forming the first gelled alginate layer so as to completely cover the first side of the collagen matrix, the first cell layer, and the structural support; and
forming a second gelled alginate layer so as to completely cover the second side of the collagen matrix.

The present invention further provides a process for forming a cellular device of the invention, comprising:
forming the first cell layer on the first side of the collagen matrix;
forming the first gelled alginate layer so as to completely cover the first side of the collagen matrix and the first cell layer;
placing the structural support on the second side of the collagen matrix; and
forming a second gelled alginate layer so as to completely cover the second side of the collagen matrix and the structural support.

In some embodiments, the process comprises:
forming the first cell layer on the first side of the collagen matrix;
forming the first gelled alginate layer so as to completely cover the first side of the collagen matrix and the first cell layer;
forming the second cell layer on the second side of the collagen matrix; and
forming a second gelled alginate layer so as to completely cover the second side of the collagen matrix and the second cell layer.

The present invention further provides a process for forming a cellular device of the invention, comprising:
forming the first cell layer on the first side of the collagen matrix;
forming the first gelled alginate layer so as to completely cover the first side of the collagen matrix and the first cell layer;
forming the second cell layer on the second side of the collagen matrix;
placing the structural support on the second cell layer; and
forming a second gelled alginate layer so as to completely cover the second side of the collagen matrix, the second cell layer, and the structural support.

The present invention further provides a process for forming a cellular device of the invention, comprising:
treating the first side of a chemically treated, lyophilized, and sterilized collagen matrix with a suspension of pancreatic islet cells to form a first cell layer, wherein the collagen matrix has first side and a second side;
placing a mesh onto the first cell layer;
clamping the mesh to the collagen matrix;
placing a solution of an alginate onto the first side of the collagen matrix so as to completely cover the first side of the collagen matrix, the first cell layer, and the mesh;
gelling the solution of an alginate to form a first gelled alginate layer by contacting with a solution of about comprises about 50 mM to about 200 mM calcium ions;
washing the first gelled alginate layer with a calcium-free solution;
placing a solution of an alginate onto the second side of the collagen matrix;
gelling the solution of an alginate to form a second gelled alginate layer by immersing in a solution of about comprises about 50 mM to about 200 mM calcium ions;
washing the second gelled alginate layer with a calcium-free solution; and
after forming the first and second gelled alginate layers, equilibrating the cellular device in a solution of 1.8 mM calcium ions.

The present invention further provides a method of implanting a cellular device, comprising implanting one or more cellular devices of the invention in a patient need thereof.

The present invention further provides a method of treating diabetes or regulating blood glucose levels in a patient in need thereof, comprising implanting one or more cellular devices of the invention, wherein the first cell layer comprises pancreatic islet cells. In some embodiments, the patient suffers from Type I diabetes.

The present invention further provides a cellular device of the invention for use in a method of treating diabetes or regulating blood glucose levels, wherein the first cell layer comprises pancreatic islet cells.

The present invention further provides a method of treating hypoparathyroidism or regulating blood calcium levels in a patient in need thereof, comprising implanting one or more cellular devices of the invention, wherein the first cell layer comprises parathyroid cells or tissue.

The present invention further provides a cellular device of the invention for use in a method of treating hypoparathyroidism or regulating blood calcium levels, wherein the first cell layer comprises parathyroid cells or tissue.

The present invention further provides a cellular device for use in a method of treatment of the human or animal body by therapy.

The present invention further provides a kit for implanting one or more devices in a patient in need thereof, comprising one or more cellular devices.

The present invention further provides a kit for use in a method of treatment of diabetes or regulating blood glucose levels comprising one or more devices, wherein the first cell layer comprises pancreatic islet cells.

The present invention further provides a kit for use in a method of treatment of hypoparathyroidism or regulating blood calcium levels comprising one or more devices, wherein the first cell layer comprises parathyroid cells or tissue.

DETAILED DESCRIPTION OF THE INVENTION

Definitions

As used herein, the term "about" means plus or minus 10% of the value.

As used herein, the term "alginate" refers to salts of alginic acid. Alginic acid, which is isolated from seaweed, is a polyuronic acid made up of two uronic acids: D-mannuronic acid and L-guluronic acid. The ratio of mannuronic acid and guluronic acid varies with factors such as seaweed species, plant age, and part of the seaweed (e.g., stem, leaf). Alginic acid is substantially insoluble in water. It forms water-soluble salts with alkali metals, such as sodium, potassium, and, lithium; magnesium; ammonium; and the substituted ammonium cations derived from lower amines, such as methyl amine, ethanol amine, diethanol amine, and triethanol amine. The salts are soluble in aqueous media above pH 4, but are converted to alginic acid when the pH is lowered below about pH 4. A thermo-irreversible water-insoluble alginate gel is formed in the presence of gel-forming ions, e.g. calcium, barium, strontium, zinc, copper(+2), aluminum, and mixtures thereof, at appropriate concentrations. The alginate gels can be solubilized by soaking in a solution of soluble cations or chelating agents for the gel-forming ions, for example EDTA, citrate and the like.

Water-insoluble alginate salts, in which the principal cation is calcium are found in the fronds and stems of seaweeds of the class Phaeophyceae, examples of which are *Fucus vesiculosus, Fucus spiralis, Ascophyllum nodosum, Macrocystis pyrifera, Alaria esculenta, Eclonia maxima, Lessonia nigrescens, Lessonia trabeculata, Laminaria japonica, Durvillea antarctica, Laminaria hyperborea, Laminaria longicruris, Laminaria digitata, Laminaria saccharina, Laminaria cloustoni*, and *Saragassum* sp. Methods for the recovery of alginic acid and its water-soluble salts, especially sodium alginate, from natural sources are well known, and are described, for example, in Green, U.S. Pat. No. 2,036,934, and Le Gloahec, U.S. Pat. No. 2,128,551. Suitable alginates include, but are not limited to, the Pronova UP and SLM series (NovaMatrix, FMC Corp., Oslo, Norway).

As used herein, the term "alginate polymer" refers to an alginate, modified alginate, or combination thereof.

As used herein, the term "modified alginate" includes alginates covalently linked to organic moieties or peptide. For example, alginate may be reacted with an organic moiety like alkylene oxide, such as ethylene oxide or propylene oxide, to form a glycol alginate. The glycol is bonded to the alginate through the carboxyl groups. Typically, alginate is reacted with propylene oxide to form propylene glycol alginate (PGA). Preparation of propylene glycol alginate is disclosed in Strong, U.S. Pat. No. 3,948,881, Pettitt, U.S. Pat. No. 3,772,266, and Steiner, U.S. Pat. No. 2,426,125. Preferably, the propylene glycol alginate has a degree of esterification of about 40% to about 95%, more preferably about 70% to 95%. Mixtures of propylene glycol alginates of different molecular weights may also be used. Aluminum ions are suitable for gelling glycol alginates.

Suitable peptides for attachment to the modified alginates include cell adhesion sequences, including a peptide having one or more RGD sequences. In some embodiments, the modified alginate comprises an alginate covalently linked to at least one cell adhesion peptide. In some embodiments, the modified alginate comprises an alginate covalently linked to at least one cell adhesion peptide, wherein the cell adhesion peptide comprises RGD. In some embodiments, cell adhesion peptides comprise RGD, YIGSR (SEQ ID NO:1), IKVAV (SEQ ID NO:2), REDV (SEQ ID NO:3), DGEA (SEQ ID NO:4), VGVAPG (SEQ ID NO:5), GRGDS (SEQ ID NO:6), LDV, RGDV (SEQ ID NO:7), PDSGR (SEQ ID NO:8), RYVLPR (SEQ ID NO:9), LGTIPG (SEQ ID NO:10), LAG, RGDS (SEQ ID NO:11), RGDF (SEQ ID NO:12), HHLGALQAGDV (SEQ ID NO:13), VTCG (SEQ ID NO:14), SDGD (SEQ ID NO:15), GREDVY (SEQ ID NO:16), GRGDY (SEQ ID NO:17), GRGDSP (SEQ ID NO:18), VAPG (SEQ ID NO:19), GGGGRGDSP (SEQ ID NO:20) and GGGGRGDY (SEQ ID NO:21) and FTLCFD (SEQ ID NO:22). Biologically active molecules for cell adhesion or other cellular interaction may include EGF, VEGF, b-FGF, FGF, TGF, TGF-β or proteoglycans. Cell attachment peptides comprising RGD may be in some embodiments, 3, 4, 5, 6, 7, 8, 9 or 10 amino acids in length. Suitable cell adhesion peptides comprising RGD include, but are not limited, to Novatach RGD (NovaMatrix, FMC BioPolymer, Oslo, Norway) and those disclosed in U.S. Pat. No. 6,642,363, which is hereby incorporated by reference in its entirety. Peptide synthesis services are available from numerous companies, including Commonwealth Biotechnologies, Inc. of Richmond, Va., USA. Chemical techniques for coupling peptides to the alginate backbones may be found in U.S. Pat. No. 6,642,363.

As used herein, the term "an RGD peptide coupled alginate" refers to an alginate which is covalently linked to a peptide comprising RGD. Suitable RGD peptide coupled alginates include, but are not limited, to Novatach RGD (NovaMatrix, FMC BioPolymer, Oslo, Norway) and those disclosed in U.S. Pat. No. 6,642,363, which is hereby incorporated by reference in its entirety.

As used herein, the term "gelled alginate layer" refers to an alginate hydrogel comprising an alginate, modified alginate, or mixture thereof, and gel-forming ions. Preferably, the alginate polymer is crosslinked by the gel-forming ions.

As used herein, the term "cell layer" refers to cells deposited on one side of the collagen matrix, which may be partially absorbed by the collagen matrix, and wherein the cells may be individual cells, clusters or spheroids of cells, or tissue fragments. In some embodiments, the cell layer is a monolayer.

As used herein, the term "clip" refers to any type of fastener used that can be used to secure the collagen matrix to the structural support including, but not limited to, clips, clamps, screws, or staples. In some embodiments, two or more clips may be used. In some embodiments, the clip is a single faster around the edges of the device. In some embodiments, the clip or clips are coated with the gelled alginate layer.

As used herein, the term "clamping" refers to secure or fasten the collagen matrix to the structural support with one or more clips.

As used herein, the term "collagen matrix" refers to a collagen material which is is a continuous sheet of material composed of collagen.

As used herein, the term "completely covers", in the context of the first and second gelled alginate layers, means that the alginate layer covers the surface such that there are no visible gaps in the coverage, or such that there is no loss in immunogenicity of the cellular device.

As used herein, the term "equilibrates" means to immerse in a medium for some length of time.

As used herein, the term "fasting blood glucose" refers to the glucose level of the blood after the patient has fasted for eight hours.

As used herein, the term "gel-forming ions" refers to ions that are capable of forming a gel with the alginate, modified alginate, or combination thereof, or which do not form a soluble salt with the alginate, modified alginate, or combination thereof. In some embodiments, the gel-forming ions comprise calcium, strontium, or barium ions, or mixtures thereof.

As used herein, the term "gelling sites" refers to functional groups on the alginate, or modified alginate that can interact with the gel-forming ions through ionic bonding to facilitate the formation of a gel. For example, an alginate has gelling sites which are carboxylate groups which can interact with gel-forming ions such calcium ions.

As used herein, the term "immersing" refers to placing the object into a liquid medium or washing the objecting the object with a liquid medium.

As used herein, the term "liquid medium" includes, but is not limited to solvents, solutions, and suspensions.

As used herein, the term "material derived from fascia lata" refers to a fascia lata that has been treated to make it suitable for implantation, for example, by removing loose connective tissue and defatting the material.

As used herein, the term "human fascia lata" refers to fascia lata from a human being. In some embodiments, the fascia lata is extracted from a cadaver or a living person.

As used herein, the term "patient" refers to any animal, including mammals, preferably monkeys, mice, rats, other rodents, rabbits, dogs, cats, swine, cattle, sheep, horses, or primates, and most preferably humans. In some embodiments, the patient is an adult, child, or infant. In some embodiments, the patient is a mammal. In some embodiments, the individual is a human.

As used herein, the term "permeable to nutrients" means that oxygen, proteins, and nutrients essential to the survival of the particular cells may pass through the structural support.

As used herein, the term "regulating blood glucose levels" means maintaining blood glucose levels within the parameters for an normal, non-diabetic individual of similar age and weight.

As used herein, the term "regulating blood calcium levels" means maintaining blood calcium levels within the parameters for an normal individual of similar age and weight.

As used herein, the term "structural support" refers to a material that imparts extra physical integrity to the device.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

In one aspect, the present invention provides a cellular device comprising:
(a) a collagen matrix having a first side and a second side;
(b) a first cell layer absorbed onto the first side of the collagen matrix; and
(c) a first gelled alginate layer and a second gelled alginate layer; wherein the first gelled alginate layer completely covers the first side of the collagen matrix and the first cell layer; and wherein the second gelled alginate layer completely covers the second side of the collagen matrix.

In some embodiments, the cellular device is sterilized. In some embodiments, the cellular device is sterilized by gamma radiation. In some embodiments, the sterilization comprises γ-irradiation, E-beam, ethylene oxide, autoclaving or contacting the device with alcohol prior to addition of the liquid component or contacting with NOx gases, hydrogen gas plasma sterilization.

In some embodiments, the cellular device posses a low content of endotoxins. In some embodiments, the cellular device possess an endotoxin level of less than 100 EU/g, less than 90 EU/g, less than 80 EU/g, less than 70 EU/g, less than 60 EU/g, less than 50 EU/g, less than 40 EU/g, less than 30 EU/g, less than 20 EU/g, less than 10 EU/g, less than 5 EU/g, or less than 1 EU/g.

In some embodiments, the alginate or modified alginate of the first or second gelled alginate layer is sterilized. In some embodiments, the alginate or modified alginate of the first or second gelled alginate layer is sterilized by gamma radiation. In some embodiments, the sterilization comprises γ-irradiation, E-beam, ethylene oxide, autoclaving or contacting the device with alcohol prior to addition of the liquid component or contacting with NOx gases, hydrogen gas plasma sterilization.

In some embodiments, the alginate or modified alginate of the first or second gelled alginate layer posseses a low content of endotoxins. In some embodiments, the alginate or modified alginate of the first or second gelled alginate layer posseses an endotoxin level of less than 100 EU/g, less than 90 EU/g, less than 80 EU/g, less than 70 EU/g, less than 60 EU/g, less than 50 EU/g, less than 40 EU/g, less than 30 EU/g, less than 20 EU/g, less than 10 EU/g, less than 5 EU/g, or less than 1 EU/g.

In some embodiments, the cellular device further comprises a second cell layer absorbed onto the second side of the collagen matrix, wherein the second gelled alginate layer completely covers the second cell layer.

A wide variety of cells appropriate for use in accordance with the cellular devices described herein, as will be readily appreciated by one of skill in the art of cell implantation. Appropriate cells (autologous, allogeneic, xenogeneic) include, for example, hepatocytes, all types of stem cells, insulin producing cells including cells derived from stem cells of any origin (e.g., pancreatic islet cells, isolated pancreatic beta cells, insulinoma cells, etc.), endocrine hormone-producing cells (e.g., parathyroid, thyroid, adrenal, etc.) and any genetically engineered cells that secrete therapeutic agents, such as proteins or hormones for treating disease or other conditions, and genetically engineered cells that secrete diagnostic agents. In some embodiments, the protein comprises factor VIII (coagulation factor VIII). In some embodiments, the first cell layer comprises pancreatic islet cells, hepatic cells, neural cells, vascular endothelial cells, thyroid cells, adrenal cells, thymic cells and ovarian cells. In some embodiments, the first cell layer comprises cells are selected from the group consisting of pancreatic islet cells, mesenchymal stem cells, parathyroid cells, and thyroid cells. In some embodiments, the first cell layer comprises cells are selected from the group consisting of pancreatic islet cells and parathyroid cells. In some embodiments, the first cell layer comprises pancreatic islet cells. In some embodiments, the first cell layer comprises mesenchymal stem cells genetically modified to express growth factor or coagulation factor VIII. In some embodiments, the first cell layer comprises mesenchymal stem cells. In some embodiments, the first cell layer comprises tissue of any of the cells described herein. In some embodiments, the second cell layer can independently comprise any of the embodiments listed herein for the cells.

In some embodiments, the cells comprise cells from a human or pig. In some embodiments, the cells comprise cells from a human, neonatal pig, or an adult pig. In some embodiments, the cells comprise cells from a human. In some embodiments, the cells comprise cells from a neonatal pig, or an adult pig. In some embodiments, the cells comprise cells from a neonatal pig. In some embodiments, the cells comprise cells from an adult pig. In some embodiments, the pancreatic islet cells comprise cells from a human or pig. In some embodiments, the pancreatic islet cells comprise cells from a human, neonatal pig, or an adult pig. In some embodiments, the pancreatic islet cells comprise cells from a human. In some embodiments, the pancreatic islet cells comprise cells from a neonatal pig, or an adult pig. In some embodiments, the pancreatic islet cells comprise cells from a neonatal pig. In some embodiments, the pancreatic islet cells comprise cells from an adult pig.

In some embodiments, the collagen matrix comprises a material derived from fascia lata. In some embodiments, the collagen matrix comprises a material derived from human fascia lata. For example, fascia lata from selected donors can be procured according to the common standards of the European Association of Muskulo Skeletal Transplantation (EAMST, Vienna, 1997). Donors can be selected considering a review of medial history, including risk factors for subacute spongiformencephalopathies. Minimum serological testing, which includes detection of HIV-1 and 2 and HTLV 1, B, and C hepatitis and syphilis can be performed. The use of allograft may be precluded if the results imply a risk for transmission of these agents. Procurement can be accomplished in an operating room or adequate mortuary facility. All instruments and equipment used for procurement are sterilized. The fascia lata can be washed in sterile physiological saline solution at room temperature until shipment to the tissue bank.

In general, the fascia lata is stripped of its external loose connective tissue including adipose tissue, vessels, and nerves. In some embodiments, the human collagen matrix is chemically (solvent detergents) treated as previously described in Dufrane D, et al., "Physical and chemical processing for a human dura mater substitute," Biomaterials. 2002, 23(14):2979-88, which is hereby incorporated by reference in its entirety. As used herein, the term "chemical treatment" means that the material has been subjected to chemical treatment in order to improve its suitability for implantation, for example, by defatting the material, inactivating prions, and/or improving its immunogenicity. Suitable methods for such chemical treatment are known to those of skill in the art including, but not limited to, the chemical treatment developed by the University Tissue Bank as described as follows. The ratio between the fascia lata and chemical solutions is about 0.2 g/cm$^2$ of fascia lata per L of solution. First, the pieces are extensively defatted in three baths of absolute acetone followed by two baths of 70° C. ethanol. Next, prion inactivation is obtained with sodium hydroxide (1 N) at room temperature during 1 hour. Reduction of immunogenicity was obtained by protein coagulation, nuclear acid precipitation, and cell membrane degradation with sodium chloride (7% w/v) during 1 hour and hydrogen peroxide (7% w/v) during 15 hours. After each procedure, pieces of fascia lata are intensively washed with a continuous distilled water flow (6 L/min).

In some embodiments, the collagen matrix is a material that is subjected to chemical treatment wherein the chemical treatment comprises immersing the material in a defatting solvent. In some embodiments, the collagen matrix is a material that is subjected to chemical treatment, wherein the chemical treatment comprises immersing the material in a defatting solvent; and contacting the material with a solution of base. In some embodiments, the collagen matrix is a material that is subjected to chemical treatment wherein the chemical treatment comprises:

immersing the material in a defatting solvent;
contacting the material with a solution of base; and
contacting the material with a solution of salt, oxidizing agent, or mixture thereof.

Suitable bases include, but are not limited to, strong bases such as sodium hydroxide and potassium hydroxide. Suitable defatting solvents include, but are not limited to, acetone, ethanol, or other alcohol. Suitable oxidizing agents include, but are not limited to hydrogen peroxide, organic peroxides. Suitable salts include, but are not limited to sodium chloride, potassium chloride, calcium chloride, strontium chloride, or barium chloride.

In some embodiments, the collagen matrix is sterilized. In some embodiments, the collagen matrix is a material sterilized by gamma radiation. In some embodiments, the sterilization comprises γ-irradiation, E-beam, ethylene oxide, autoclaving or contacting the foam with alcohol prior to addition of the liquid component or contacting with NOx gases, hydrogen gas plasma sterilization. In some embodiments, the collagen matrix comprises a collagen possessing a low content of endotoxins. In some embodiments, the collagen matrix comprises a material with an endotoxin content of less than 100 EU/g, less than 90 EU/g, less than 80 EU/g, less than 70 EU/g, less than 60 EU/g, less than 50 EU/g, less than 40 EU/g, less than 30 EU/g, less than 20 EU/g, less than 10 EU/g, less than 5 EU/g, or less than 1 EU/g.

In some embodiments, the collagen matrix is a material treated by lyophilization.

In some embodiments, the collagen matrix is from about 0.1 mm to about 3 mm, from about 0.1 mm to about 2 mm, from about 0.5 mm to about 2 mm, from about 0.5 mm to about 1.5 mm in thickness.

In some embodiments, the first gelled alginate layer and second gelled alginate layer each independently comprises an alginate with a weight-average molecular weight of about 4 kD to about 300 kD. In some embodiments, the first gelled alginate layer and second gelled alginate layer each independently comprises an alginate with a weight-average molecular weight of about 50 kD to about 300 kD, about 150 kD to about 250 kD, about 75 kD to about 150 kD, or about 10 kD to about 75 kD. In some embodiments, the first gelled alginate layer and second gelled alginate layer each independently comprises an alginate with a weight-average molecular weight of less than about 75 kD, less than about 50 kD, or less than about 40 kD.

In some embodiments, the first gelled alginate layer and the second gelled alginate layer each independently comprises an alginate with a mannuaronate to guluronate ratio equal to or greater than about 1. In some embodiments, the first gelled alginate layer and the second gelled alginate layer comprises an alginate derived from *macrocystitis purifera*.

In some embodiments, the first gelled alginate layer and the second gelled alginate layer each independently comprises an alginate, modified alginate, or mixture thereof. In some embodiments, the first gelled alginate layer and the second gelled alginate layer each independently comprises an alginate. In some embodiments, the first gelled alginate layer and the second gelled alginate layer each independently comprises a modified alginate. In some embodiments, the first gelled alginate layer and the second gelled alginate layer each independently comprises an alginate modified with a cell adhesion sequence. In some embodiments, the first gelled alginate layer and the second gelled alginate layer each independently comprises a RGD peptide coupled alginate.

In some embodiments, the first gelled alginate layer and second gelled alginate layer each independently comprise multivalent cations. In some embodiments, the first gelled alginate layer and second gelled alginate layer each independently comprise strontium ions, barium ions, calcium ions, or mixture thereof. In some embodiments, the first gelled alginate layer and second gelled alginate layer each independently comprise calcium ions.

In some embodiments, the ratio of alginate to calcium ions on each side of the cellular device comprises about 1.5 mL to about 2.5 mL of a 3% solution of alginate per $cm^2$ for each 30 mL of 100 mM solution of calcium ions.

In some embodiments, the first gelled or second alginate layer each independently comprise from about 0.01 g to about 1 g, about 0.01 to about 0.9 g, about 0.01 to about 0.8 g, about 0.01 to about 0.7 g, about 0.01 g to about 0.6 g, about 0.01 g to about 0.5 g, about 0.01 g to about 0.4 g, about 0.01 g to about 0.3 g, about 0.01 to about 0.2 g, or about 0.02 g to about 0.2 g of alginate polymer per $cm^2$.

In some embodiments, the first or second gelled alginate layer each independently comprises about 0.5% w/v to about 7% w/v by weight of alginate. In some embodiments, the first or second gelled alginate layer each independently comprises about 1% w/v to about 7% w/v by weight of alginate. In some embodiments, the first or second gelled alginate layer each independently comprises about 2% w/v to about 6% w/v by weight of alginate. In some embodiments, the first or second gelled alginate layer each independently comprises about 3% w/v to about 5% w/v by weight of alginate. In some embodiments, the first or second gelled alginate layer each independently comprises about 2.5% w/v to about 3.5% w/v by weight of alginate. In some embodiments, the first or second gelled alginate layer each independently comprises about 4.5% w/v to about 5.5% w/v by weight of alginate. In some embodiments, the first or second gelled alginate layer each independently comprises about 3% w/v by weight of alginate. In some embodiments, the first or second gelled alginate layer each independently comprises about 5% w/v by weight of alginate. In some embodiments, the first or second gelled alginate layer each independently comprises about 5% w/v by weight of Pronova $SLM_{20}$ (NovaMatrix, FMC Biopolymer, Norway. In some embodiments, the first or second gelled alginate layer each independently comprises about 5% w/v by weight of Pronova $SLM_{100}$ (NovaMatrix, FMC Biopolymer, Norway).

In some embodiments, the cellular device is equilibrated in a solution comprising a physiological concentration of gel-forming ions. In some embodiments, the cellular device is equilibrated in a solution comprising a physiological concentration of calcium ions. In some embodiments, the cellular device is equilibrated in a solution comprising about 1.8 mM calcium ions.

In some embodiments, each side of the cellular device has an area of about 1 $cm^2$ to about 4 $cm^2$, 0.5 $cm^2$ to about 3 $cm^2$, 1 $cm^2$ to about 3 $cm^2$, 0.5 $cm^2$ to about 2 $cm^2$, 1 $cm^2$ to about 2 $cm^2$, or 0.5 $cm^2$ to about 2.5 $cm^2$. In some embodiments, each side of the cellular device has an area of about 1 $cm^2$.

In some embodiments, the cellular device further comprises a structural support. The structural support may provide the cellular device with improved physical integrity, which may then improve the length of time the device remains viable after implantation. Further, improvements in physical integrity may allow for better retrieval of the device after implantation. The structural support may be made of any material that will impart better physical integrity to the device. In some embodiments, the structural support is polyester. The structural support may be placed onto either side of the device, or may surround the edges of the device. In some embodiments, the first or second gelled alginate layer completely covers the structural support, if necessary in order to impart immunogenicity.

In some embodiments, the cellular device further comprises a structural support placed onto the first cell layer; wherein:
the first gelled alginate layer completely covers the structural support; and
the structural support is permeable to nutrients.

In some embodiments, a structural support placed onto the second side of the collagen matrix, wherein the second gelled alginate layer completely covers the structural support. In some embodiments, the cellular device further comprises a structural support placed onto the second cell layer, wherein:
the second gelled alginate layer completely covers the structural support; and
the structural support is permeable to nutrients.

The structural support may provide the cellular device with improved physical integrity, which may then improve the length of time the device remains viable after implantation. Further, improvements in physical integrity may allow for better retrieval of the device after implantation. The structural support may be made of any material that will impart better physical integrity to the device. In some embodiments, the structural support is polyester.

When the structural support covers the side of the collagen matrix containing a cell layer, the support should be designed to enable the passage of nutrients to the cell layer. In some embodiments, the structural support comprises a mesh.

In some embodiments, the mesh has a mesh opening of about 10 μm to about 1 mm. In some embodiments, the mesh has a mesh opening of about 20 μm to about 500 μm. In some embodiments, the mesh has a mesh opening of about 300 μm.

In some embodiments, the cellular device further comprises one or more clips affixing the structural support to the collagen matrix. In some embodiments, the cellular device further comprises one or more clips affixing the structural support to the collagen matrix. In some embodiments, the cellular device further comprises two or more clips affixing the structural support to the collagen matrix.

It is known that failure of encapsulated devices due to stability issues can result in destruction of the device by lymphocytes and macrophages and fibrosis. For example, in a primate study (Dufrane et al, Transplantation vol 81, 9: 2006: pg 1345), it has been demonstrated that >92% of encapsulated islets are not characterized by cellular overgrowth and 13% of capsule are broken at 180 days post-transplantation. This indicates that most of capsules containing pig islets are retrieved at 6 months post-transplantation without any immunosuppression demonstrating stability of capsules. If capsules are not stable, immunological reaction is induced and most of capsules are destroyed by lymphocytes and macrophages and fibrosis. Similarly, in a Wistar rats model (Dufrane et al. Biomaterials 2006, vol 27: pg 3201), it has been demonstrated that >91% of the initial volume of capsules is retrieved after 30 days post-implantation in subcutaneous tissues as well as in the kidney capsule spaces. In contrast, after implantation into the peritoneum, only 67% of the initial volume was found due to capsule fibrosis. Hence, when a device is unstable, there may be significant problems in retrieving the device from the patients.

In some embodiments, the cellular device is retrievable. As used herein in this particular context, the term "retrievable" means that less than about 10% of the cellular devices are broken or display signs of fibrosis after 30 days or longer. In some embodiments, less than about 10% of the cellular devices are broken or display signs of fibrosis after 60 days or longer. In some embodiments, less than about 10% of the cellular devices are broken or display signs of fibrosis after 90 days or longer.

In some embodiments, the first and second gelled alginate layers are not degradable.

In some embodiments, the first and second gelled alginate layers do not degrade in physiological fluid at physiological temperatures after one month. In this context, "do not degrade in physiological fluid" means that less than 80% by weight of the alginate does dissolves under the physiological conditions.

In some embodiments:
said collagen matrix comprises a material derived from human fascia lata; and
said first gelled alginate layer and second gelled alginate layer each independently comprise a RGD coupled alginate and multivalent cations selected from the group consisting of calcium ions, barium ions, strontium ions or combination thereof.

In some embodiments:
the collagen matrix comprises a material derived from fascia lata; and
the first gelled alginate layer and second gelled alginate layer each independently comprise multivalent cations selected from the group consisting of calcium ions, barium ions, strontium ions or combination thereof.

In some embodiments:
the collagen matrix comprises a material derived from human fascia lata; and
the first gelled alginate layer and second gelled alginate layer each independently comprise multivalent cations selected from the group consisting of calcium ions, barium ions, strontium ions or combination thereof.

In some embodiments:
the collagen matrix comprises a material derived from fascia lata; and
the first gelled alginate layer and second gelled alginate layer each independently comprise an alginate and multivalent cations selected from the group consisting of calcium ions, barium ions, strontium ions or combination thereof.

In some embodiments:
the collagen matrix comprises a material derived from human fascia lata; and
the first gelled alginate layer and second gelled alginate layer each independently comprise an alginate and multivalent cations selected from the group consisting of calcium ions, barium ions, strontium ions or combination thereof.

In some embodiments:
the collagen matrix comprises a material derived from human fascia lata; and
the first gelled alginate layer and second gelled alginate layer each independently comprise a modified alginate and multivalent cations selected from the group consisting of calcium ions, barium ions, strontium ions or combination thereof.

In some embodiments:
the collagen matrix comprises a material derived from human fascia lata; and
the first gelled alginate layer and second gelled alginate layer each independently comprises calcium ions and an alginate with a weight-average molecular weight of about 75 kD to about 150 kD.

In some embodiments:
the collagen matrix comprises a material derived from human fascia lata; and
the first gelled alginate layer and second gelled alginate layer each independently comprises calcium ions and an alginate with a weight-average molecular weight of less than about 75 kD.

In some embodiments:
the collagen matrix comprises a material derived from human fascia lata; and
the first gelled alginate layer and second gelled alginate layer each independently comprises calcium ions and an alginate with a weight-average molecular weight of less than about 50 kD.

In some embodiments:
the collagen matrix comprises a material derived from human fascia lata; and
the first gelled alginate layer and second gelled alginate layer each independently comprises calcium ions and an alginate with a weight-average molecular weight of less than about 40 kD.

In some embodiments:
the collagen matrix comprises a material derived from human fascia lata; and
the first gelled alginate layer and second gelled alginate layer each independently comprise calcium ions.

In some embodiments:
the collagen matrix comprises a material derived from human fascia lata; and
the first gelled alginate layer and second gelled alginate layer each independently comprises an calcium ions and an alginate with a weight-average molecular weight of about 4 kD to about 300 kD.

In some embodiments:
a structural support placed onto the first cell layer; and
one or more clips affix the structural support to the collagen matrix;
wherein:
the collagen matrix comprises a material derived from human fascia lata;
the gelled alginate layer and second gelled alginate layer each independently comprise calcium ions; and
the first gelled alginate layer completely covers the structural support and is permeable to nutrients.

In some embodiments:
the collagen matrix comprises a material derived from human fascia lata;
the first cell layer comprises about 20,000 to about 40,000 pancreatic islet cells;
the first gelled alginate layer and second gelled alginate layer each independently comprises calcium ions and an alginate with a weight-average molecular weight of about 4 kD to about 300 kD;

the cellular device is equilibrated in a solution comprising about 1.8 mM calcium ions;

a structural support placed onto the first cell layer; and one or more clips affix the structural support to the collagen matrix;

wherein:

the collagen matrix comprises a material derived from human fascia lata;

the gelled alginate layer and second gelled alginate layer each independently comprise calcium ions;

the first gelled alginate layer completely covers the structural support and is permeable to nutrients; and the structural support comprises a polyester mesh.

In some embodiments:

a structural support placed onto said first cell layer;

two or more clips affix said structural support to said collagen matrix;

wherein:

said collagen matrix comprises a material derived from human fascia lata;

said gelled alginate layer and second gelled alginate layer each independently comprise calcium ions; and said first gelled alginate layer completely covers said structural support and is permeable to nutrients.

In some embodiments:

the collagen matrix comprises a material derived from human fascia lata;

the first cell layer comprises about 20,000 to about 40,000 pancreatic islet cells;

the first gelled alginate layer and second gelled alginate layer each independently comprises calcium ions and an alginate with a weight-average molecular weight of about 4 kD to about 300 kD;

the cellular device is equilibrated in a solution comprising about 1.8 mM calcium ions;

a structural support placed onto the first cell layer; and two or more clips affix the structural support to the collagen matrix;

wherein:

the collagen matrix comprises a material derived from human fascia lata;

the gelled alginate layer and second gelled alginate layer each independently comprise calcium ions;

the first gelled alginate layer completely covers the structural support and is permeable to nutrients; and the structural support comprises a polyester mesh.

Process for Forming a Cellular Device and Products of these Processes

The processes herein may be used to produce any of the embodiments of the cellular devices hereinbefore described, including various combinations and subcombinations of the embodiments.

The present invention further provides a process for forming a cellular device of the invention, comprising:

forming the first cell layer on the first side of the collagen matrix;

forming the first gelled alginate layer so as to completely cover the first side of the collagen matrix and the first cell layer; and forming a second gelled alginate layer so as to completely cover the second side of the collagen matrix.

In some embodiments, the process further comprises placing the structural support on the first cell layer or on said second side of said collagen matrix, provided that said structural support is permeable to nutrients and said first or said second gelled alginate layer completely cover said structural support.

In some embodiments, the process comprises:

forming the first cell layer on the first side of the collagen matrix;

placing the structural support on the first cell layer;

forming the first gelled alginate layer so as to completely cover the first side of the collagen matrix, the first cell layer, and the structural support; and forming a second gelled alginate layer so as to completely cover the second side of the collagen matrix.

In some embodiments, the process comprises:

forming the first cell layer on the first side of the collagen matrix;

forming the first gelled alginate layer so as to completely cover the first side of the collagen matrix and the first cell layer;

placing the structural support on the second side of the collagen matrix; and forming a second gelled alginate layer so as to completely cover the second side of the collagen matrix and the structural support.

In some embodiments, the process comprises:

forming the first cell layer on the first side of the collagen matrix;

forming the first gelled alginate layer so as to completely cover the first side of the collagen matrix and the first cell layer;

forming the second cell layer on the second side of the collagen matrix; and forming a second gelled alginate layer so as to completely cover the second side of the collagen matrix and the second cell layer.

In some embodiments, the process comprises:

forming the first cell layer on the first side of the collagen matrix;

forming the first gelled alginate layer so as to completely cover the first side of the collagen matrix and the first cell layer;

forming the second cell layer on the second side of the collagen matrix;

placing the structural support on the second cell layer; and forming a second gelled alginate layer so as to completely cover the second side of the collagen matrix, the second cell layer, and the structural support.

In some embodiments, the process comprises:

treating the first side of a chemically treated, lyophilized, and sterilized collagen matrix with a suspension of pancreatic islet cells to form a first cell layer, wherein the collagen matrix has first side and a second side;

placing a mesh onto the first cell layer;

clamping the mesh to the collagen matrix;

placing a solution of an alginate onto the first side of the collagen matrix so as to completely cover the first side of the collagen matrix, the first cell layer, and the mesh;

gelling the solution of an alginate to form a first gelled alginate layer by contacting with a solution of about comprises about 50 mM to about 200 mM calcium ions;

washing the first gelled alginate layer with a calcium-free solution;

placing a solution of an alginate onto the second side of the collagen matrix;

gelling the solution of an alginate to form a second gelled alginate layer by immersing in a solution of about comprises about 50 mM to about 200 mM calcium ions;

washing the second gelled alginate layer with a calcium-free solution; and after forming the first and second gelled alginate layers, equilibrating the cellular device in a solution of 1.8 mM calcium ions.

In some embodiments of the processes, the first gelled alginate layer is formed by the steps of:

placing a solution of an alginate onto the first side of the collagen matrix so as to completely cover first side of the collagen matrix and the first cell layer; and gelling the solution of an alginate by contacting the alginate solution with a solution of gel-forming ions;

(ii) the second gelled alginate layer is formed by the steps of:

placing a solution of an alginate onto the second side of the collagen matrix so as to completely cover the second side of the collagen matrix; and gelling the solution of an alginate by contacting the alginate solution with a solution of gel-forming ions.

A salt or combination of salts that provides the desired gel-forming ions or mixture of gel-forming ions may be used as the gel-forming ions. Suitable gel-forming ions for forming each gelled layer include multivalent cations, preferably a divalent and/or a trivalent cations. For alginates, suitable polyvalent cations include, for example, calcium(2+), barium (2+), strontium(2+), iron(2+), zinc(2+), copper(2+), and aluminum(3+). Preferred cations are divalent metal cations, more preferably the calcium (2+) cation. In some embodiments, the gel-forming ions in selected from the group consisting of strontium ions, barium ions, calcium ions, and combination thereof.

The concentration of gel-forming ions required to saturate 100% of the gelling sites of the alginate polymer can be calculated by well-known principles. For example, when sufficient gel-forming ions, such as calcium ion, are present to react with all available gelling sites (eg. the L-guluronic acid units in the case of alginate), the alginate is 100% saturated. The amount of cation required to completely saturate the gelling sites of alginate, for example, is considered to be 1 mole of divalent cation per 2 moles of L-guluronic acid in the alginate or 1 mole of trivalent cation per 3 moles of L-guluronic acid in the alginate when only a divalent cation or only a trivalent cation is used in the gelling. When a mixture of a divalent cation or cations and a trivalent cation or cations is used, the amounts required to saturate the alginate can be determined because a divalent cation occupies two gelling sites and a trivalent cation occupies three gelling sites. Thus, any amount less than this is considered to be an amount less than that required to completely saturate the gelling sites of the alginate.

For alginate, the strength of gels formed by reaction of alginate with polyvalent cations is related to the molecular weight of the alginate, the guluronic acid content ("G content") of the alginate as well as the arrangement of guluronic and mannuronic acids on the polymer chain. In some embodiments, the G content of the alginate for the gel is suitably at least about 30%, about 40% to about 90%, or about 50% to about 80%. Alginate derived from, for example, *Lessonia trabeculata* and from the stems of *Laminaria hyperborea* have a high G content.

The amount of divalent cation, such as calcium, required to react stoichiometrically with these G-blocks can be calculated for each alginate type by considering that two guluronic acid units plus one divalent cation are required to create one ionic crosslink. The amount of calcium required for stoichiometric saturation of a 1% sodium alginate solution are given in the following table:

| Seaweed Source | % G | mM Ca |
| --- | --- | --- |
| *Laminaria hyperborea* (stem) | 70 | 14-16 |
| *Laminaria hyperborea* (leaf) | 54 | 11-13 |
| *Lessonia trabeculata* | 68 | 13-15 |
| *Macrocystis pyrifera* | 39 | 8-9 |

A list of various commercially available alginates, their properties, and their sources is found in Shapiro, U.S. Pat. No. 6,334,968, Table 1, column 16, line 49, to column 17, line 18, which is hereby incorporated herein by reference in its entirety. Mixtures or blends of alginates, for example alginates of different molecular weights and/or G content, may be used to form the first or second gelled alginate layer.

Complete saturation (100% saturation) of the gelling sites occurs when the composition contains 1 mole of divalent cation per 2 moles of L-guluronic acid units. For example, an about 15 mM solution of calcium ion is required to 100% saturate a 1% solution of sodium alginate extracted from the stems of *Laminaria hyperborea*, an about 12 mM calcium solution is required to 100% saturate a 1% solution of sodium alginate extracted from the leaves (fronds) of *Laminaria hyperborea*, and an about 14 mM solution of calcium ions is required to 100% saturate a 1% solution of sodium alginate extracted from *Lessonia trabeculata*.

In some embodiments, each of the processes further comprises clamping the structural support to the collagen matrix.

In some embodiments, the solution of gel-forming ions comprises about 50 mM to about 200 mM gel-forming ions. In some embodiments, the solution of gel-forming ions comprises about 100 mM gel-forming ions.

In some embodiments, each of the processes further comprises washing the cellular device in a solution free of gel-forming ions after forming the first gelled alginate layer and the second gelled alginate layer.

In some embodiments, each of the processes further comprises equilibrating the cellular device in a 1.8 mM solution of calcium ions after processing. In some embodiments, each of the processes further comprises equilibrating the cellular device in a solution comprising a physiological concentration of multivalent cations after processing.

The present invention further comprises products of the processes described herein.

Methods of Using the Cellular Devices

The methods and uses may utilize all of the embodiments of the cellular devices and the products of the processes hereinbefore described, including various combinations and subcombinations of the embodiments.

The present invention provides a method of implanting a cellular device, comprising implanting one or more cellular devices of the invention in a patient need thereof. The technique described herein can be used for a variety of different cell types as described herein. The type of cell chosen will vary with the particular therapeutic use. The cellular devices can be implanted by a variety of methods known to one of skill in the art. For example, the cellular devices may be implanted by various methods known to those of skill in the art, such as subcutaneously or surgically into various organs, muscles, tissues, or lumen of an organ. The cellular devices can be implanted into various tissues including, but not limited to, retroperitoneum, properitoneal space, mesentery, renal subcapular space, peritoneum, and intramuscular space.

In some embodiments, the one or more cellular devices are implanted subcutaneously. In some embodiments, three to four cellular devices are implanted into the patient.

In some embodiments, less than about 10% of the cellular devices were broken about 6, 7, 8, 9, 10, 11, 12, 13, 14, 15 weeks after the implanting. In some embodiments, less than about 10% of the cellular devices do not show signs of fibrosis after 6, 7, 8, 9, 10, 11, 12, 13, 14, 15, 16, 17, 18, 19, 20, 21, or 22 weeks post implantation.

In some embodiments, a therapeutically effective number of cells are implanted. The number of cells needed for the treatment of a specific disorder will vary depending the specific disorder(s) being treated, the size, age, and response pattern of the individual the severity of the disorder(s), the judgment of the attending clinician, the manner of administration, and the purpose of the administration, such as prophylaxis or therapy. The phrase "effective amount" refers to the number of cells that elicits the biological or medicinal response in a tissue, system, animal, individual, patient, or human that is being sought by a researcher, veterinarian, medical doctor or other clinician. The desired biological or medicinal response may include preventing the disorder in an individual (e.g., preventing the disorder in an individual that may be predisposed to the disorder, but does not yet experience or display the pathology or symptomatology of the disease). The desired biological or medicinal response may also include inhibiting the disorder in an individual that is experiencing or displaying the pathology or symptomatology of the disorder (i.e., arresting or slowing further development of the pathology and/or symptomatology). The desired biological or medicinal response may also include ameliorating the disorder in an individual that is experiencing or displaying the pathology or symptomatology of the disease (i.e., reversing the pathology or symptomatology).

Theoretically, the number of islet cells required to achieve insulin independence is about 10,000 islets per kg of body fat for a human diabetic recipient. However, it is known that 100,000 cells, approximately 10% of the total islet number in a normal human pancreas, is required to achieve blood glucose control. It is believed that subcutaneous transplantation of the cellular devices of the invention can significantly reduce the number of islets required to achieve blood glucose control.

One or more devices can be implanted in a patient to reach a therapeutically effective amount of cells. In addition, the number of cells may be divided between a first cell layer and a second cell layer if so desired. In some embodiments, the first cell layer or, optionally, the second cell layer each independently comprises about 5,000 cells or more. In some embodiments, the first cell layer comprises from about 5,000 to about 300,000 cells, about 5,000 to about 200,000 cells, about 5,000 to about 100,000 cells, about 10,000 to about 100,000 cells, about 5,000 to about 60,000 cells, about 10,000 to about 60,000 cells, about 20,000 to about 60,000, or about 20,000 to about 40,000 cells. In some embodiments, the second cell layer comprises about from 5,000 to about 300,000 cells, about 5,000 to about 200,000 cells, about 5,000 to about 100,000 cells, about 10,000 to about 100,000 cells, about 5,000 to about 60,000 cells, about 10,000 to about 60,000 cells, about 20,000 to about 60,000, or about 20,000 to about 40,000 cells. In some embodiments, the first cell layer comprises about 5,000 to about 300,000 cells, about 5,000 to about 200,000 cells, about 5,000 to about 100,000 cells, about 10,000 to about 100,000 cells, about 5,000 to about 60,000 cells, about 10,000 to about 60,000 cells, about 20,000 to about 60,000, or about 20,000 to about 40,000 cells per $cm^2$. In some embodiments, the second cell layer comprises about 5,000 to about 300,000 cells, about 5,000 to about 200,000 cells, about 5,000 to about 100,000 cells, about 10,000 to about 100,000 cells, about 5,000 to about 60,000 cells, about 10,000 to about 60,000 cells, about 20,000 to about 60,000, or about 20,000 to about 40,000 cells per $cm^2$.

In some embodiments, three to four cellular devices are implanted into the patient, wherein the cell layer comprises pancreatic islet cells.

The present invention further provides a method of treating diabetes or regulating blood glucose levels in a patient in need thereof, comprising implanting one or more cellular devices of the invention, wherein the first cell layer comprises pancreatic islet cells. The present invention further provides a cellular device of the invention for use in a method of treating diabetes or regulating blood glucose levels, wherein the first cell layer comprises pancreatic islet cells.

In some embodiments, the fasting blood glucose levels of the patient are controlled for ten weeks or more. In some embodiments, the fasting blood glucose levels of the patient are controlled for up to twenty-four weeks.

The present invention further provides a method of treating hypoparathyroidism or regulating blood calcium levels in a patient in need thereof, comprising implanting one or more cellular devices of the invention, wherein the first cell layer comprises parathyroid cells or tissue. The present invention further provides a cellular device of the invention for use in a method of treating hypoparathyroidism or regulating blood calcium levels, wherein the first cell layer comprises parathyroid cells or tissue.

In some embodiments, no PERV contamination was observed after about 1, 2, 3, 4, 5, 6, 7, 8, 9, or 10 weeks of implantation, wherein the first cell layer comprises cells derived from pigs.

The present invention further provides a cellular device for use in a method of treatment of the human or animal body by therapy.

The present invention further provides a kit for implanting one or more devices in a patient in need thereof, comprising one or more cellular devices.

The present invention further provides a kit for use in a method of treatment of diabetes or regulating blood glucose levels comprising one or more devices, wherein the first cell layer comprises pancreatic islet cells.

The present invention further provides a kit for use in a method of treatment of hypoparathyroidism or regulating blood calcium levels comprising one or more devices, wherein the first cell layer comprises parathyroid cells or tissue.

EXAMPLES

In order that the invention disclosed herein may be more efficiently understood, examples are provided below. It should be understood that these examples are for illustrative purposes only and are not to be construed as limiting the invention in any manner.

Example 1

Isolation Pig Pancreatic Islet Cells

Adult pig pancreases were harvested from Landrace pigs (>200 kg, n=10) at the local slaughterhouse (Centre A. de Marbaix, Louvain-la-Neuve, Mr. Collignon) and islets were isolated as follows. Isolation and purification techniques were described in sections of Dufrane D, et al., "Impact of porcine islet size on cellular structure and engraftment after transplantation: adult versus young pigs", Pancreas. 2005, 30(2): 138-47; and Dufrane D. et al., "Parameters favouring successful adult pig islet isolations for xenotransplantation in "pigto-primate" model," Xenotranplantation., 2006, 13:1-11, each of which is hereby incorporated by reference in its entirety.

Pancreas tails from adult pig donors were digested by a modified static digestion method as described by O'Neil, et al., "The isolation and function of porcine islets from market weight pigs," Cell Transplant. 2001, 10:235-246, which is hereby incorporated by reference in its entirety. The pancreas was infused with a 2 to 3-fold volume (ml/gr) of Liberase PI (Roche/Boerhinger Mannheim, 0.5 mg/ml) dissolved in modified UW-M solution. The pancreas was injected in order to achieve an adequate distension, placed in a sterile 1 liter Nalgene jar and digested by static incubation at 37° C. for 50 min. Digestion was terminated by addition of Ham-F10+20% NCS based on the visual inspection of the gland. The cell suspension was filtered through a stainless steel mesh with a pore size of 1000 µm and diluted in Ham-F10+20% NCS. Following previous data obtained in human islet isolation, digested tissue was passed over a bed of 6-mm glass beads and through a 500 stainless-steel mesh screen. The tissue effluent was collected with 3 to 4 L of cold Ham-F10+10% NCS in 250 ml conical tubes and centrifuged at 700 rpm at 4° C. Islets, cells and debris collected after the pre-purification column (8 tubes on average) were then centrifuged at 4° C. (630 g for 3 minutes). All cellular pellets were pooled in one tube and suspended in 200 mL Ham-F10 medium. From this suspension, 100 µL aliquots were taken to evaluate the results of the digestion after dithizone staining (see Isolation outcome). Cells were then centrifuged at 4° C. (280 g for 5 min), the supernatant was removed and cells were suspended in 75 mL Ficoll Eurocollins (Mediatech, Hemdon, USA) solutions for purification in gradient tubes (ref: nalg3122-0250; VWR International, Leuven, Belgium).

Islets isolated with the static method were purified, at 4° C. on a discontinuous Ficoll Euro-Collins gradient. The post-digestion cellular pellet, suspended in 75 mL of Ficoll Euro-Collins solution (density=1.1 g/cm$^3$), was placed in a flat-bottom tube. Lower gradients of Ficoll were then added sequentially (50 mL of 1,096 g/cm$^3$; 50 mL of 1,060 g/cm$^3$ and 20 ml of Ham-F10 medium). After centrifugation of the gradient tubes at 856 g for 17 min, islets were collected from the 1.1/1.096 and 1.096/1.060 interfaces. Islets from each interface were suspended in 2 tubes containing 50 mL Ham-F10+10% NCS serum. The tubes were centrifuged at 280 g for 3 minutes, the supernatant was removed and the cells were washed with 150 mL Ham-F10 medium. This procedure was repeated 3 times and, finally, the islets were suspended in 200 mL Ham-F10 medium for isolation outcome study.

Example 2

Preparation of a Cellular Device Comprising Pig Islets and Preparation of Comparative Capsules of Pig Islets Comparative Capsule Preparation:

Capsules containing pig islets were prepared for comparison purposes. Freshly isolated pig islets were encapsulated in an SLM 100 alginate matrix (Batch 110064, FMC BioPolymer, Drammen, Norway) containing a high concentration of mannuronic acid (High-M, 56%). Freeze-dried alginate (viscosity: 174 mPa·s; endotoxin <25 EU/gram), was diluted in a MOPS 1× washing buffer (Inotech Encapsulation AG, Dottikon, Switzerland) at a concentration of 1% w/v. Pig islet cells were suspended in alginate at a concentration of 10,000 islet cells/mL and encapsulation was performed by the Inotech Encapsulation AG device (serial number: LS-01.005; Dottikon, Switzerland).

Quality of capsule was microscopically evaluated (on 100 capsules samples) in order to determine the capsule diameter and the percentage of non-well shaped and broken capsules (see FIG. 1).

Cellular Device Preparation:

Fascia lata from selected donors can be procured according to the common standards of the European Association of Muskulo Skeletal Transplantation (EAMST, Vienna, 1997). Donors can be selected considering a review of medial history, including risk factors for subacute spongiformencephalopathies. Minimum serological testing, which includes detection of HIV-1 and 2 and HTLV 1, B, and C hepatitis and syphilis can be performed. The use of allograft may be precluded if the results imply a risk for transmission of these agents. Procurement can be accomplished in an operating room or adequate mortuary facility. All instruments and equipment used for procurement are sterilized. The fascia lata can be washed in sterile physiological saline solution at room temperature until shipment to the tissue bank.

The fascia lata was mechanically tripped of its external loose connective tissue including adipose tissue, vessels and nerves. The remaining material was cut into very small pieces (1 cm$^2$) and washed by pulse lavage. The human collagen matrix was chemically (solvent detergents) and physically (Gamma irradiation) treated as previously described in Dufrane D, et al., "Physical and chemical processing for a human dura mater substitute," Biomaterials. 2002, 23(14):2979-88, which is hereby incorporated by reference in its entirety. The chemical treatment developed by the University Tissue Bank was composed by a succession of multiple steps. The ratio between the fascia lata and chemical solutions was 0.2 g/cm$^2$ of fascia lata per L of solution. First, the pieces were extensively defatted in three baths of absolute acetone followed by two baths of 70° C. ethanol. Next, prion inactivation was obtained with sodium hydroxide (1 N) at room temperature during 1 hour. Reduction of immunogenicity was obtained by protein coagulation, nuclear acid precipitation, and cell membrane degradation with sodium chloride (7% w/v) during 1 hour and hydrogen perioxide (7% w/v) during 15 hours. After each procedure, pieces of fascia lata were intensively washed with a continuous distilled water flow (6 L/min). Allografts were further freeze-dried for three consecutive days (working vacuum 1×10$^{-6}$ Hg, shelf temperature of −30° C. and condenser temperature of −196° C.). The final residual moisture, as previously measured on other samples (by gravimetric analysis at 100° C.) for the same freeze dyer was <1% of the final dry weight. Tissue was packed in a doubled plastic bag and sterilized by gamma radiation at 25,000 Gy (IBA Mediris, Fleurus, Belgium). Then, graft was stored at room temperature.

Freshly isolated pig islets were placed on a lyophilised human treated collagen matrix. A Polyester Filters (300 µm mesh opening, Spectrum Laboratories Inc, C.A., U.S.A.) was placed over cellular layer and fixed by Titanium clip (Ethicon Endo surgery Inc; Johnson and Johnson Company, OH, USA). SLM 100 alginate matrix (BATCH 304051; FMC BioPolymer, Drammen, Norway) 3% w/v was placed with a 1 mL syringe and cross-linked, during 5 minutes with CaCl$_2$ 100 mM MOPS 1× washing buffer solution (Inotech Encapsulation AG, Dottikon, Switzerland). The monolayer cellular device (MCD) was then washed twice with a calcium-free MOPS 1× buffer during 4 minutes and MCD was then placed in culture for overnight (see below). After cultivation, medium was removed and MCD was washed with calcium-free MOPS 1× buffer during 2 minutes. After cross-linking, calcium solution was removed and washed twice with MOPS 1× solution. An additional SLM alginate matrix 1 w/v was placed in contact with human collagen matrix and cross-linked as previously described. The monolayer cellular device (MCD) was then washed twice with a calcium-free MOPS 1× buffer during 4 minutes.

Culture for the Capsules and MCD Prior to Transplantion:

The best culture regime to obtain optimal stability of pig encapsulated islets was the cultivation in 17 ml CMRL 1066 at 1.8 mM $CaCl_2$ for 18 hours, in 75 $cm^2$ non-tissue culture treated flask at a concentration of 10,000 capsules 1 flask in a serum-free medium (Dufrane D., et al., "Six month survival of microencapsulated pig islets and alginate biocompatibility in primates: Proof of Concept," Transplantation, 2006, 81(9): 1345-53, which is hereby incorporated by reference in its entirety).

Example 3

Implantation of Cellular Devices Comprising Pig Islets into Cynomolgus Monkeys and Comparison to Microencapsulated Pig Islets Cynomolgus monkeys (3-6 years old: 4-6 kg) were housed according to the guidelines of the Belgian Ministry of Agriculture and Animal Care. All procedures were approved by the local Ethics Committee for Animal Care of the University Catholique de Louvain. Filter-sterilized Streptozotocin (STZ) (Sigma, Bornem, Belgium) was diluted in 100 mM sodium citrate to 25 mg/mL (pH 4.5) and administrated intravenously over 5 minutes in primates (through the femoral vein) at 50 mg/kg body weight. The hepatic function was assessed prior to, and one and 4 weeks after, STZ injection by assessment of serum aspartate aminotransferase (AST) and alanine aminotransferase (ALT) while the renal function was evaluated by plasma creatinine (Kodak Ektachem DTSC 11; Ortho-Clinical Diagnostics, INC, Rochester, N.Y., USA). The pancreatic endocrine function was evaluated at the same time-points by monitoring the fasting (overnight) serum blood glucose (FBG) and performing intra-venous glucose tolerance tests (IVGTT). The IVGTT was initiated after overnight fasting by the intravenous bolus injection of 0.5 g/kg body weight 50% w/v glucose. Blood samples were collected after glucose administration at 0, 1, 5, 10, 20, 30, 60 minutes for primates. Glucose serum concentrations were measured by Kodak Ektachem DT60 II (Ortho-Clinical Diagnostics, INC, Rochester, N.Y., USA). For each IVGTT, the area under the glucose curve (AUC) (integrated from 0 to 90 minutes) compared with the mean pre-IVGTT concentration (−5 min) and the Glucose K value (between 1 and 30 min) were calculated. Human C-peptide and insulin (for primates) levels were measured, in sera, using a radioimmunoassay (RIA) kit according to the manufacturer's protocol (Lico Research, Nuclilab BV, BB EDE, Netherlands). Dufrane D, et al., "Streptozotocin-induced diabetes in large animals (pigslprimates): role of GLUT2 transporter and beta-cell plasticity', Transplantation, 2006, 81(1):36-45, which is hereby incorporated by reference in its entirety.

Figure 4:
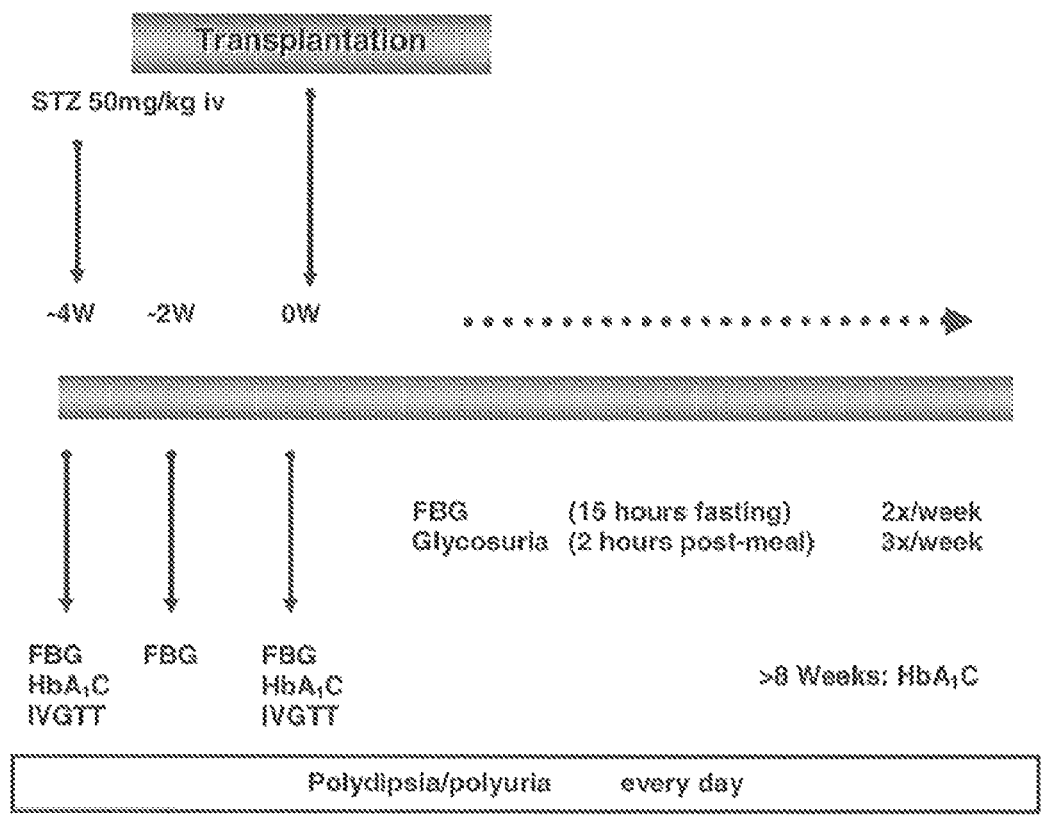
FIG. 4 depicts the protocol followed for transplantation.

All STZ-treated animals displayed clinical features of T1DM including: polyuria (range: 380-100 mL), polydipsia (range: 870-2160 mL), weight lost (a mean reduction of 27% of initial weight after 4 weeks of diabetes induction), persistent fasting hyperglycaemia (range: 153-483 mg/dl), glycosuria (1000 mg/dl), pathological intra-venous glucose tolerance test (IVGTT; for glucose absorption, insulin and C-peptide secretion) and glycosylated haemoglobin over 13%. Diabetes was induced by streptozotocin (50 mg/kg) 4-8 weeks prior to transplantation (FIG. 4).

Transplantation:

After anaesthesia, each animal received 15,000 microencapsulated islets equivalent to (IEQ)/kg of body recipient, collected in a 10 mL syringe. Positive control animals received the same number of non-encapsulated pig islets under the kidney capsule. Negative control animal received a volume of empty capsules corresponding to the volume of 15,000 EQ/kg encapsulated pig islets (a mean of 7 mL). Each graft was transplanted under the capsule of one kidney per primate.

We have demonstrated in the preclinical pig-to-primate model that simple alginate beads are able to protect adult pig islets against xeno rejection. However, we did not demonstrate that encapsulated adult pig islets might control diabetes in STZ-treated cynomolgus monkeys. Based on our previous work, we decided to transplant alginate-microencapsulated adult pig islets under the kidney capsules of STZ-induced diabetic cynomolgus monkeys.

Figure 3:
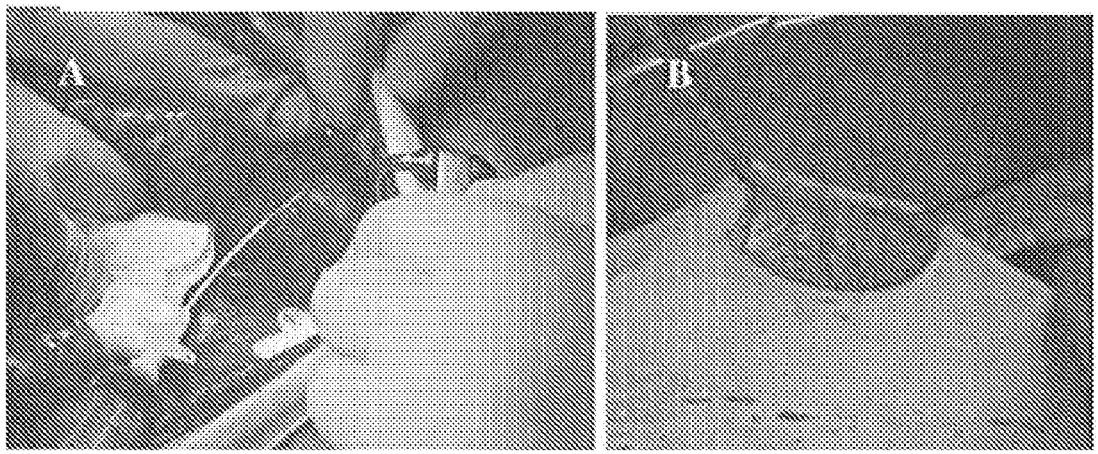
FIG. 3 depicts the transplantation of alginate-encapsulated pig islets under the kidney capsule (A) and under the skin (B).

Transplantation of alginate-encapsulated pig islets was performed under the kidney capsule of STZ-induced diabetic cynomolgus monkeys in order to compare these results with those obtained previously in non-diabetic animals (FIG. 3, A, under kidney capsule). MCD were placed subcutaneously (FIG. 3, B). Transplantation was carried out according to the protocol in FIG. 4. The experimental groups are shown below.

Experimental Groups and Protocol:
I. Positive control (Ctrl+): two animals were transplanted with 20,000 IEQ/kg of non-encapsulated pig islets under the kidney capsule.
II. Sham control: two animals were transplanted with a mean volume of 16 mL of empty alginate capsules under the kidney capsule.
III. Treated animals: four animals were transplanted with encapsulated pig islets under the kidney capsule:
   Primate 1 received 24,327 IEQ/kg corresponding to 14 mL of graft volume
   Primate 2 received 15,985 IEQ/kg corresponding to 12 mL of graft volume
   Primate 3 received 31,750 IEQ/kg corresponding to 17 mL of graft volume
   Primate 4 received 28,385 IEQ/kg corresponding to 15 mL of graft volume
IV. Treated animals: four animals were transplanted with MCD subcutaneously
   Primate 5 received 28,905 IEQ/kg corresponding to 3 MCD
   Primate 6 received 27,210 IEQ/kg corresponding to 4 MCD
   Primate 7 received 33,333 IEQ/kg corresponding to 4 MCD
   Primate 8 received 33,568 IEQ/kg corresponding to 5 MCD A: Results with Capsules Versus Control A significant elevation of FBG was observed after diabetes induction (by STZ) and prior to transplantation (FIG. 5: Week −4 until Week 0). No correction of FBG was observed for cynomolgus monkeys transplanted with empty capsules (n=2) or non-encapsulated pig islets (n=2), thereby confirming the validity of our in vivo model. In these animals, there was no correction of polyuria, polydipsia. glycosuria (1000 mg/dl) and body weight lost (−30% between Week 0 to Week 10/12). Between 10 and 12 weeks post transplantation, all animals presented glycosylated haemoglobin ($HbA_1C$) of >13%. They were then sacrificed and grafts and pancreases were removed. Empty capsules removed from sham animals did not demonstrate any foreign-body reaction and no signs of pig-islet survival were found from kidneys transplanted with non-encapsulated pig islets.

Pancreases of STZ-induced diabetic Cynomolgus were fixed and stained for insulin to determine the residual islet-volume density by histomorphometry. A mean of −97% of islet-volume density was found destroyed after more than 14 weeks of diabetes induction.

Figure 5:
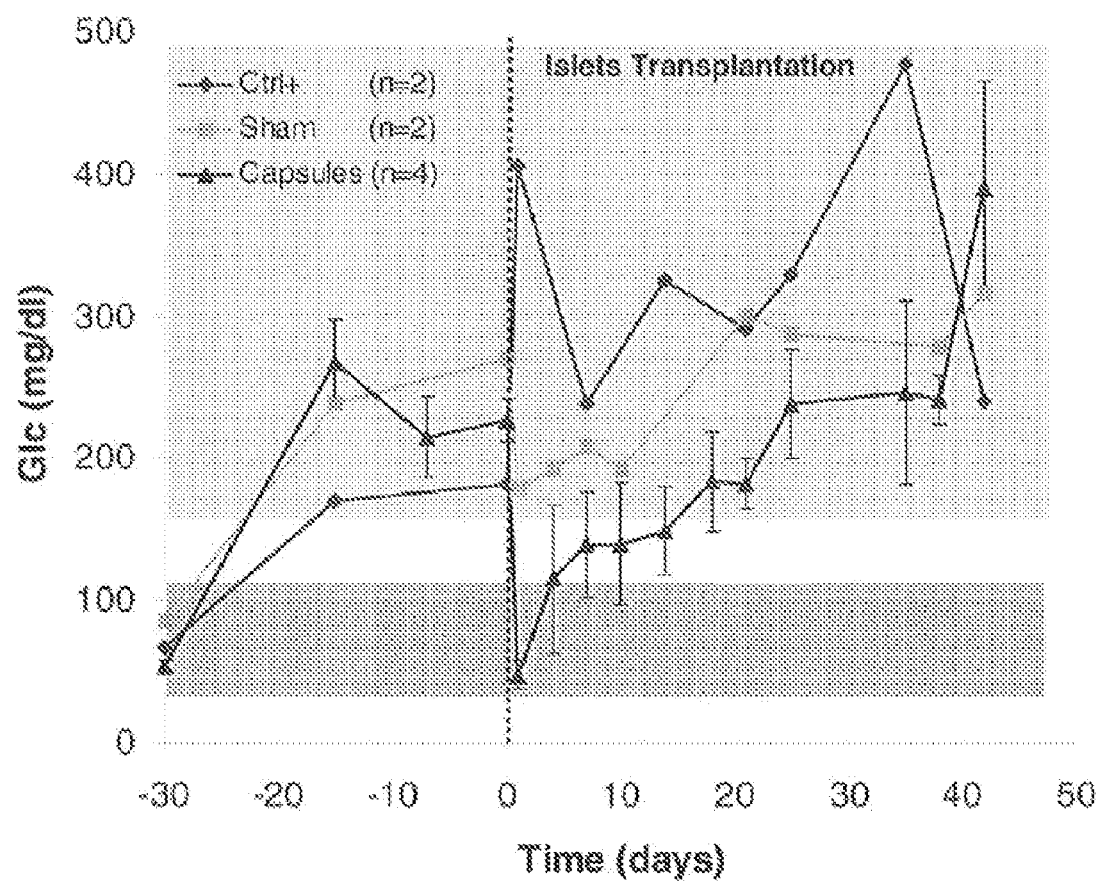
FIG. 5 depicts the fasting blood glucose (FBG) course prior and after transplantation of diabetic primates with empty capsules (sham), non-encapsulated pig islets (Ctrl+) and encapsulated pig islets (Capsules). The lighter shaded area represents the range of FBG for diabetic monkeys; the darker shaded area corresponds to the range of normoglycaemic monkeys.
Figure 6:
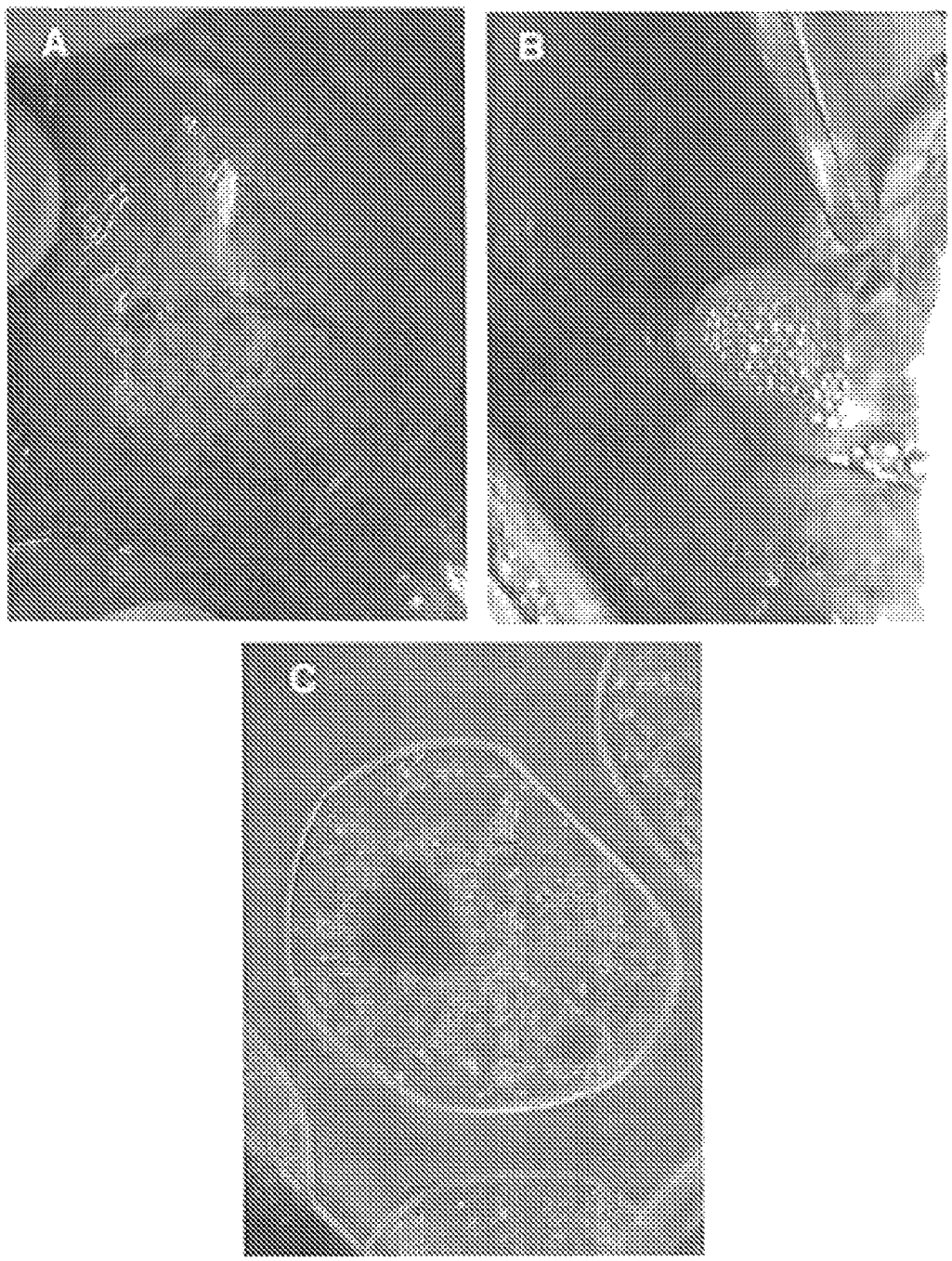
FIG. 6 depicts graft removal after 6 weeks of transplantation under the kidney capsule of diabetic primates, showing no sign of graft fibrosis (A and B). Dithyzone encapsulated pig islets were still observed after graft explantation (C).

After transplantation of encapsulated pig islets, a significant reduction of FBG was observed one week after xenotransplantation (FIG. 5). The reduction of FBG was associated in two primates (Primates 3 and 4) with a significant reduction of glycosuria during the first week post transplantation (1000 to 100 mg/dl). In addition, a significant reduction of polydipsia (−60% of volume prior to transplantation) and polyuria (−67% of volume prior to transplantation) was observed during the first week post transplantation. Between two and six weeks post transplantation, progressive elevation of FBG, polyuria, polydipsia, and glycosuria (1000 mg/dl) were observed. We then decided to remove the encapsulated pig islets after 6 weeks of transplantation in order to study the quality of graft removal. After graft explantation, no sign of graft fibrosis (FIG. 6: A, B) was observed and less than 5% of removal capsules were broken and characterized by cellular overgrowth (FIG. 6: C). A mean 60% of capsules recovered after graft explantation were composed by dithyzone islets (FIG. 6C). However, electron microscopy demonstrated central islets necrosis with cellular suffering in many capsules (data not shown). We therefore decided to develop a mono-layer macroencapsulation system based on alginate as the protecting membrane for xeno-pig islets.

Several attempts (data not shown) were needed to obtain the most appropriate design and to obtain the monolayer cellular device (MCD). Since the MCD could not be easily implanted under the kidney capsule of primates (insufficient space and risk of MCD disruption), we transplanted it in the subcutaneous space. We choose the latter as we previously showed in rats that this site is biocompatible and also because the subcutaneous space seems a clinically applicable site.

Figure 7:
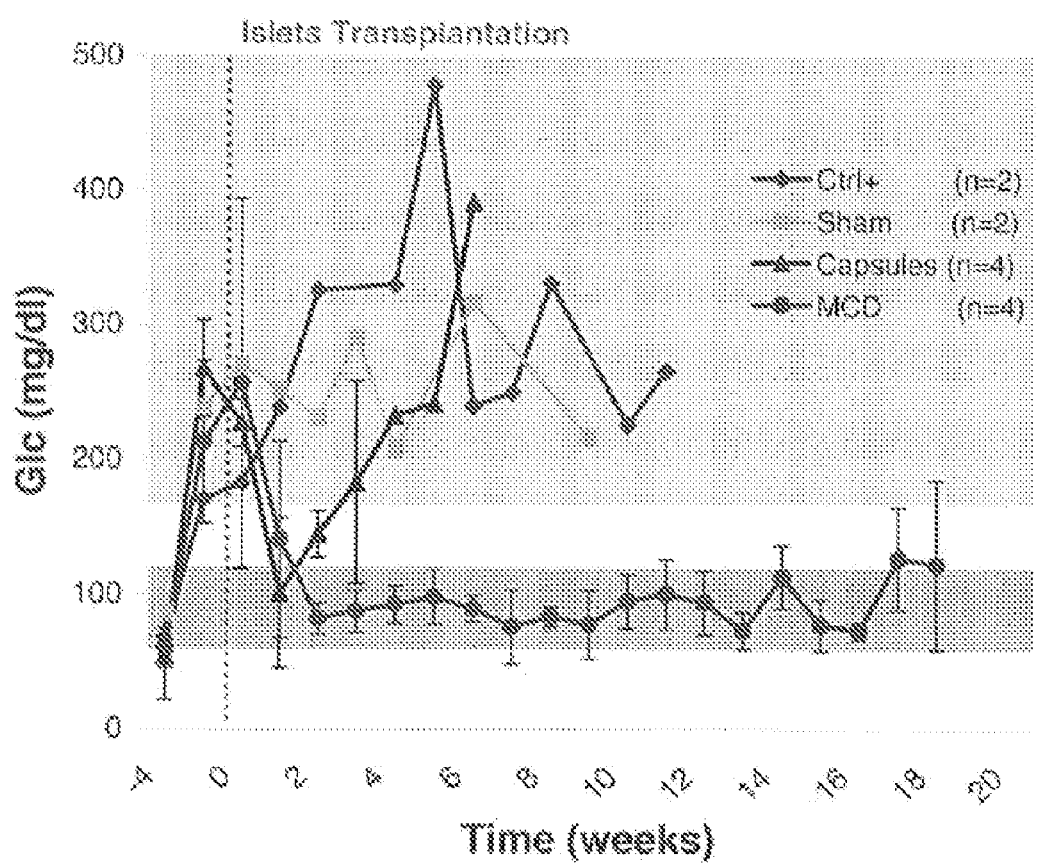
FIG. 7 depicts fasting blood glucose (FBG) course prior and after transplantation of diabetic primates with empty capsules (sham), non-encapsulated pig islets (Ctrl+), encapsulated pig islets (capsules) and monolayer cellular devices (MCD). The lighter shaded area represents the range of FBG for diabetic monkeys; the darker shaded area corresponds to the range of normoglycaernic monkeys.

B. Results with the MCD:

After transplantation, diabetes was significantly corrected for primates transplanted with MCD in contrast with those receiving encapsulated pig islets under the kidney capsule (FIG. 7). Fasting blood glucose regulation (between 48-107 mg/dl, FIG. 7), reduction of glycosuria (1000 mg/dl prior transplantation to 0 mg/dl after transplantation), and reduction of polyuria (>70%) and polydipsia (>70%) were observed.

Figure 8:
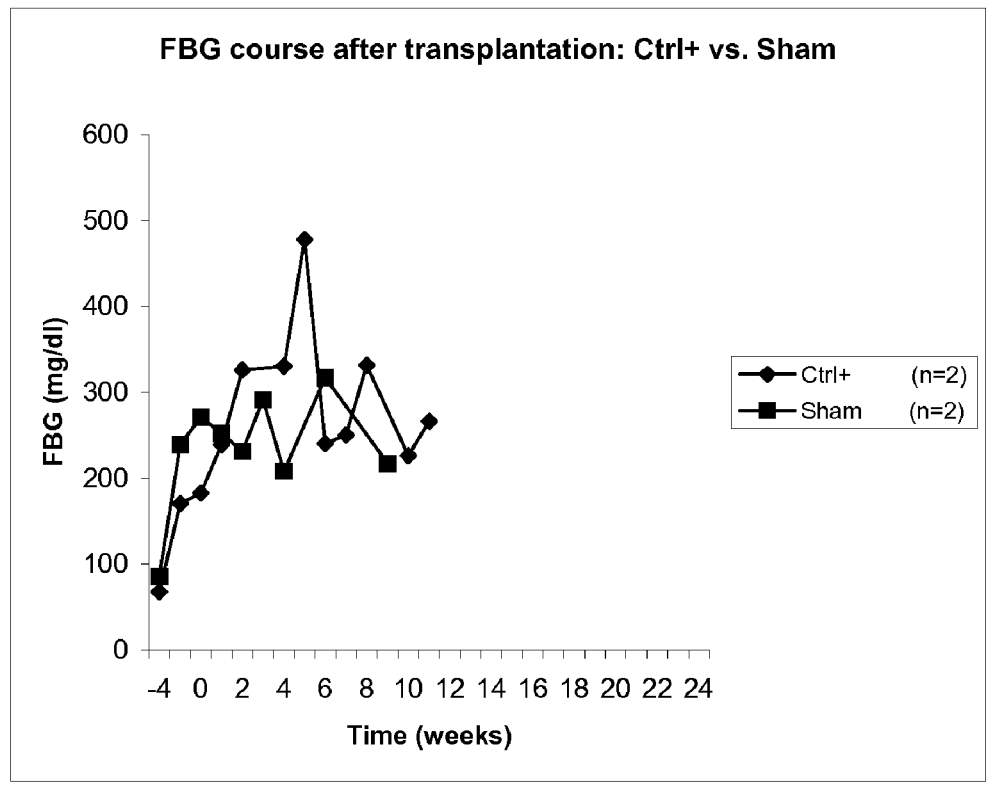
FIG. 8 depicts fasting blood course after transplantation of monolayer cellular device (Primates 5-8) versus microencapsulated pig islets (n=4) (FIG. 8, lower graph) and positive control (non-encapsulated pig islets) and empty capsule (Sham) (FIG. 8, upper graph).
Figure 8:
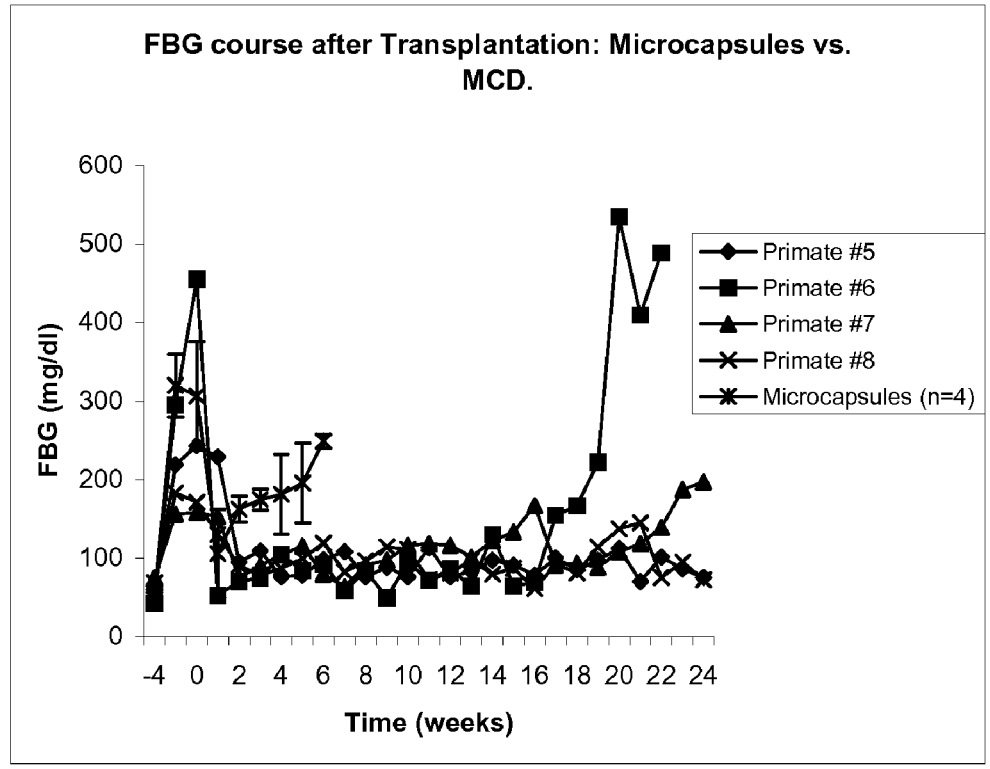

A significant improvement of diabetes control was obtained up to 24 weeks for primates transplanted with pig islets encapsulated in MCD (FIG. 8, lower). In contrast, a short fasting blood glucose control was obtained in case microencapsulated pig islets (less than 2 weeks post-transplantation) (FIG. 8, lower).

Figure 9:
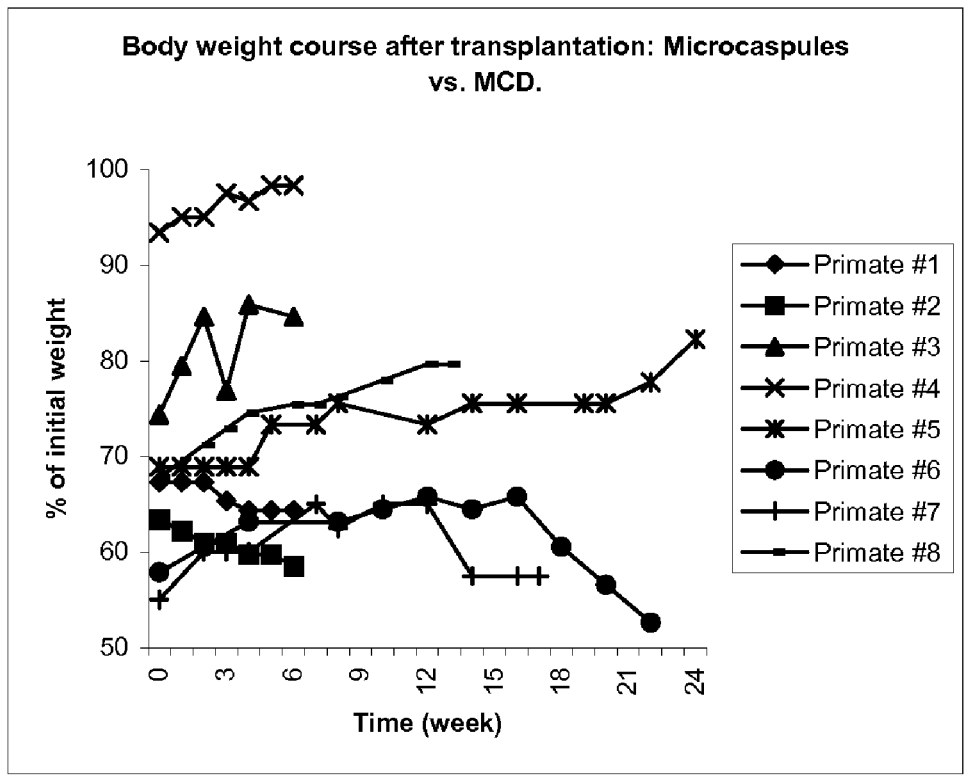
FIG. 9 depicts body weight course after transplantation of monolayer cellular device (Primates 5-8) versus microencapsulated pig islets (n=4) (FIG. 9, upper graph) and positive control (non-encapsulated pig islets) and empty capsule (Sham) (FIG. 9, lower graph).
Figure 9:
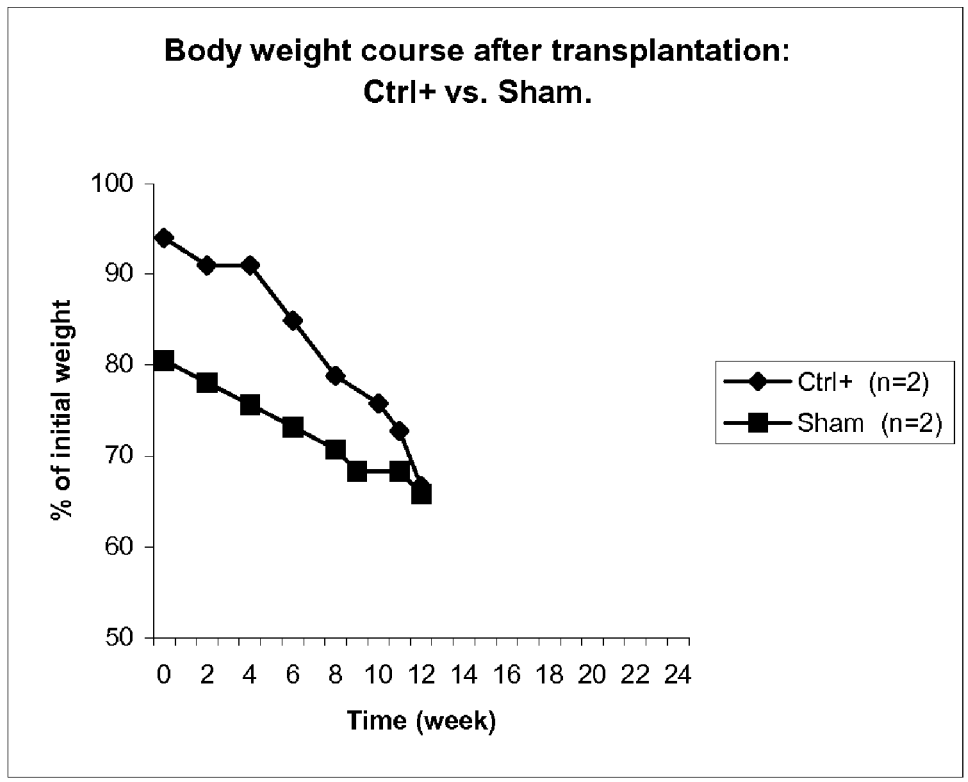

Body weight course after transplantation of MCD (Primates 5-8) versus microencapsulated pig islets (n=4) and positive control (non-encapsulated pig islets) and empty capsule (Sham) was studied (FIG. 9). A significant improvement of body weight was obtained up to 24 weeks for primates transplanted with pig islets encapsulated in MCD (FIG. 9, upper). In contrast, a short improvement of body weight was obtained in case microencapsulated pig islets (FIG. 9, upper).

Figure 10:
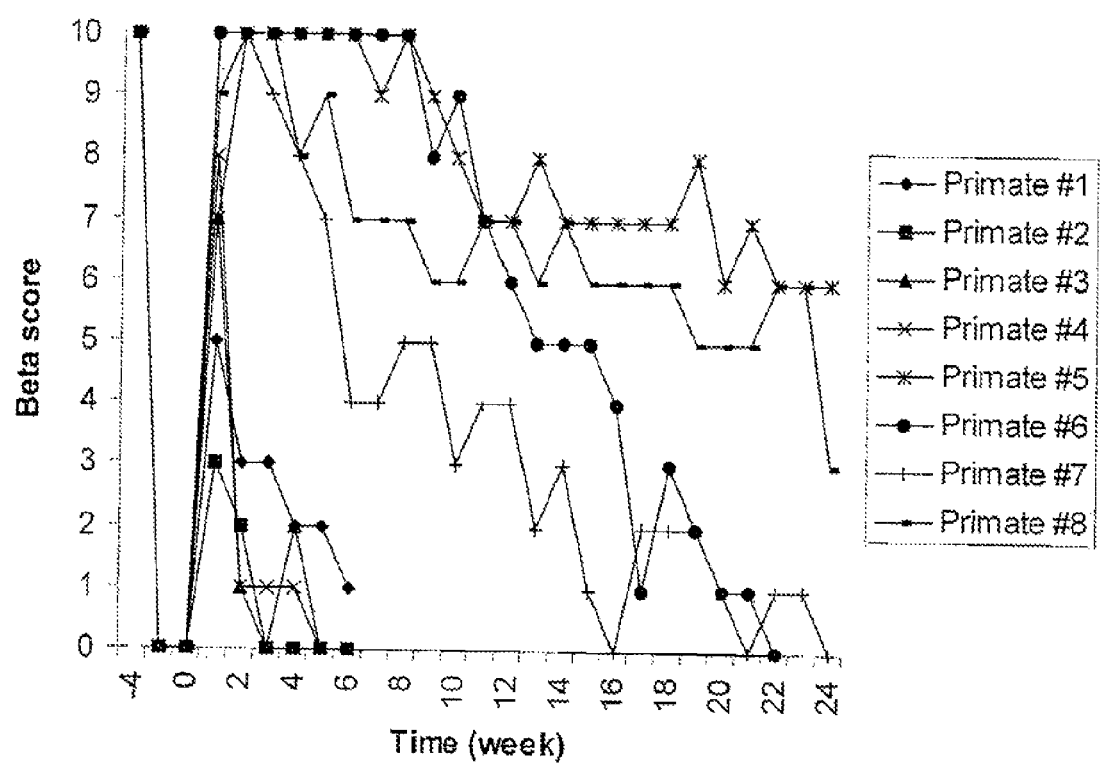
FIG. 10 depicts beta score (integrated measures of fasting blood glucose/Glycosuria 24 hrs/Glycosuria 2 h post-meal/Polyuria/Polydypsia) course after transplantation of pig islets encapsulated in MCD versus microencapsulated pig islets over 24 weeks.
Figure 11:
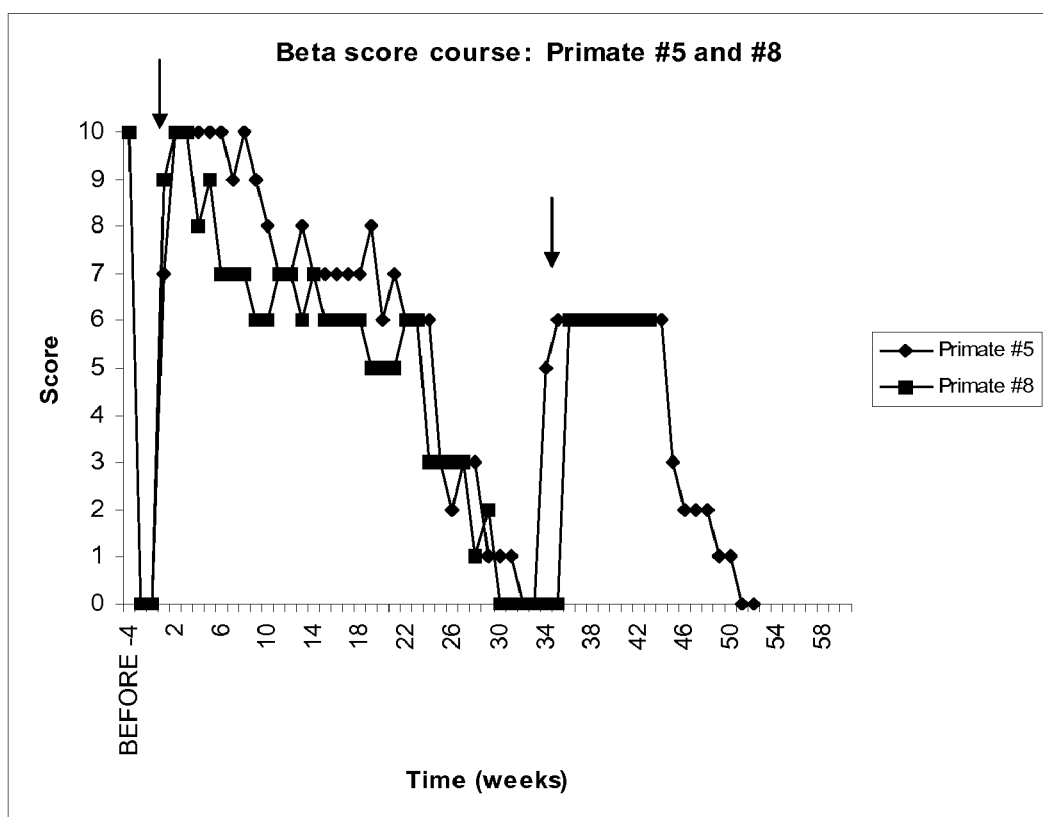
FIG. 11 depicts beta score (integrated measures of fasting blood glucose/Glycosuria 24 hrs/Glycosuria 2 h post-meal/Polyuria/Polydypsia) course after transplantation of pig islets encapsulated in MCD versus microencapsulated pig islets over 54 weeks (first arrow indicate transplantation; second arrow indicates retransplantation of primates 5 and 8).

Beta score (integrated measures of Fasting blood glucose/Glycosuria 24 hrs/Glycosuria 2 h post-meal/Polyuria/Polydypsia) course after transplantation of MCD (Primates 5-8) versus microencapsulated pig islets (Primates 1-4) was studied (FIG. 10). Prior transplantation, diabetes induction induced a significant reduction of beta-score (10 to 0 before and after diabetes induction, respectively) corresponding to diabetes with glycosuria, polyuria, polydypsia and elevated fasting blood glucose. A longer correction was obtained for MCD verus microencapsulated pig islets (FIG. 10). For example, diabetes was corrected for Primates 5 and 9 until a mean of 20 weeks post-transplantation. A gradual decline of function was observed between weeks 24 and 34 post-transplantation (FIG. 11). Then, it was decided to re-transplant exactly at the same location than the first graft. Diabetes was controlled again up to 10 weeks post-retransplantation (FIG. 11).

The $HbA_1C$ course was followed since the time of diabetes induction by STZ (FIG. 15). Normoglycaemic monkeys demonstrated a range of $HbA_1C$ between 4.8% and 7.2%. After STZ-treatment, all diabetic primates were characterized by an $HbA_1C$ of over 13% (limit of detection kit repeated 4-times prior to transplantation). No correction of $HbA_1C$ was observed until 10 to 12 weeks for primates transplanted with non-encapsulated pig islets (Ctrl+, mean of two primates) and empty capsules (sham, mean of two primates) (FIG. 15), which confirmed the absence or rejection of the islets and the diabetic status. Additional diabetic primates did not demonstrate correction of $HbA_1C$ until six months post-diabetes induction ($HbA_1C$>13%, n=4). After transplantation with encapsulated pig islets (primates 1 to 4), no $HbA_1C$ measurement after transplantation was reported since all animals were sacrificed prior to eight weeks post transplantation (FIG. 15). This decision was taken since no significant regulation of FBG was observed in these cases after transplantation (FIG. 5).

When primates were transplanted with MCD, a significant reduction of $HbA_1C$ was observed after eight weeks post transplantation (FIG. 15). This reduction was confirmed after 12 and 16 weeks post transplantation (FIG. 15) and continued up to a maximum of 24 weeks. In two cases, graft dysfunction was correlated with a re-elevation of $HbA_1C$ until 34 weeks post-transplantation. After re-transplantation (in Grey), diabetes was controlled again with a significant reduction of $HbA_1C$ (Primate 5: $HbA_1C$ of 9.6, 11.3 at 42 weeks and 48 weeks, respectively; Primate 8: $HbA_1C$ of 7.4 and 8.5 at 42 weeks and 48 weeks, respectively).

Figure 12:
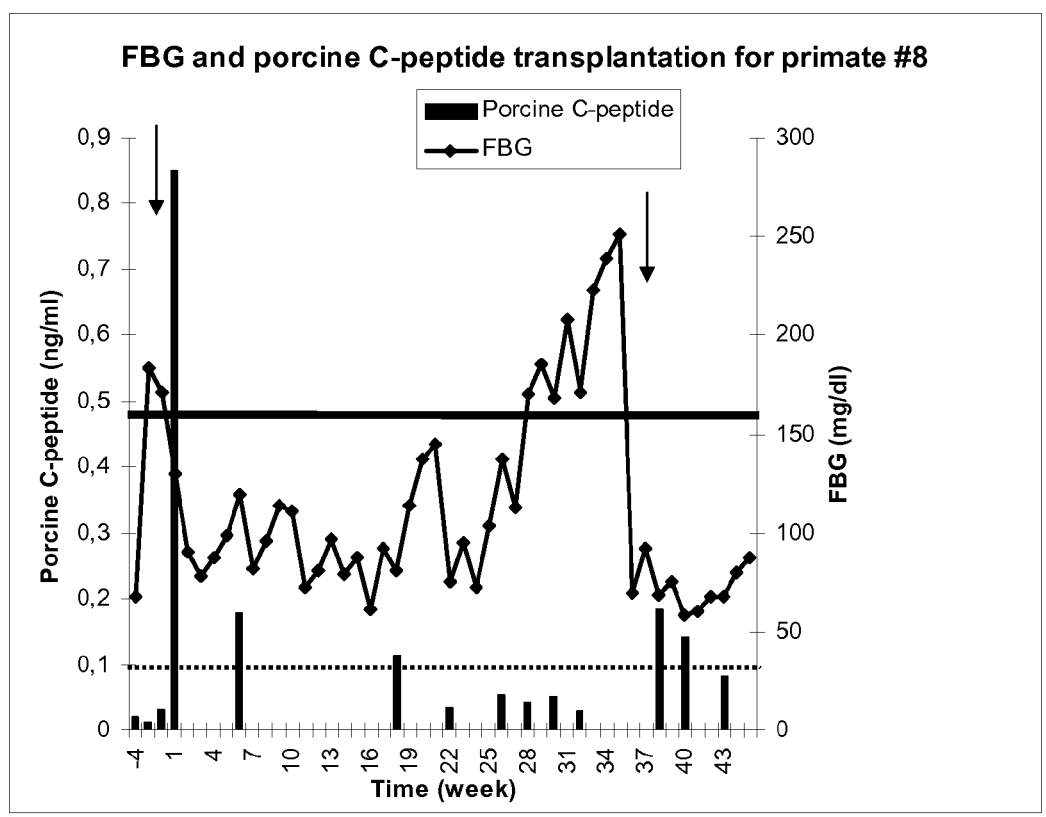
FIG. 12 depicts porcine C-peptide course and fasting blood glucose course in primate #8 after the first and second transplantation of pig islets encapsulated in MCD (first arrow indicate transplantation; second arrow indicates retransplantation of primates 5 and 8).

Porcine C-peptide course and Fasting blood glucose course in primate #8 after the first and second transplantation of pig islets encapsulated in MCD were measured (FIG. 12). Prior transplantation, diabetes induction induced a significant elevation of fasting blood glucose and no porcine C-peptide (arrow indicates graft transplantation). For this monkey, diabetes was corrected until a mean of 22 weeks post-transplantation associated with porcine C-peptide detection in the primate sera. A gradual decline of function was observed between weeks 24 and 34 post-transplantation. Then, it was decided to re-transplant exactly at the same location than the first graft. Diabetes was controlled again up to 10 weeks post-retransplantation in the presence of Porcine C-peptide.

Figure 13:
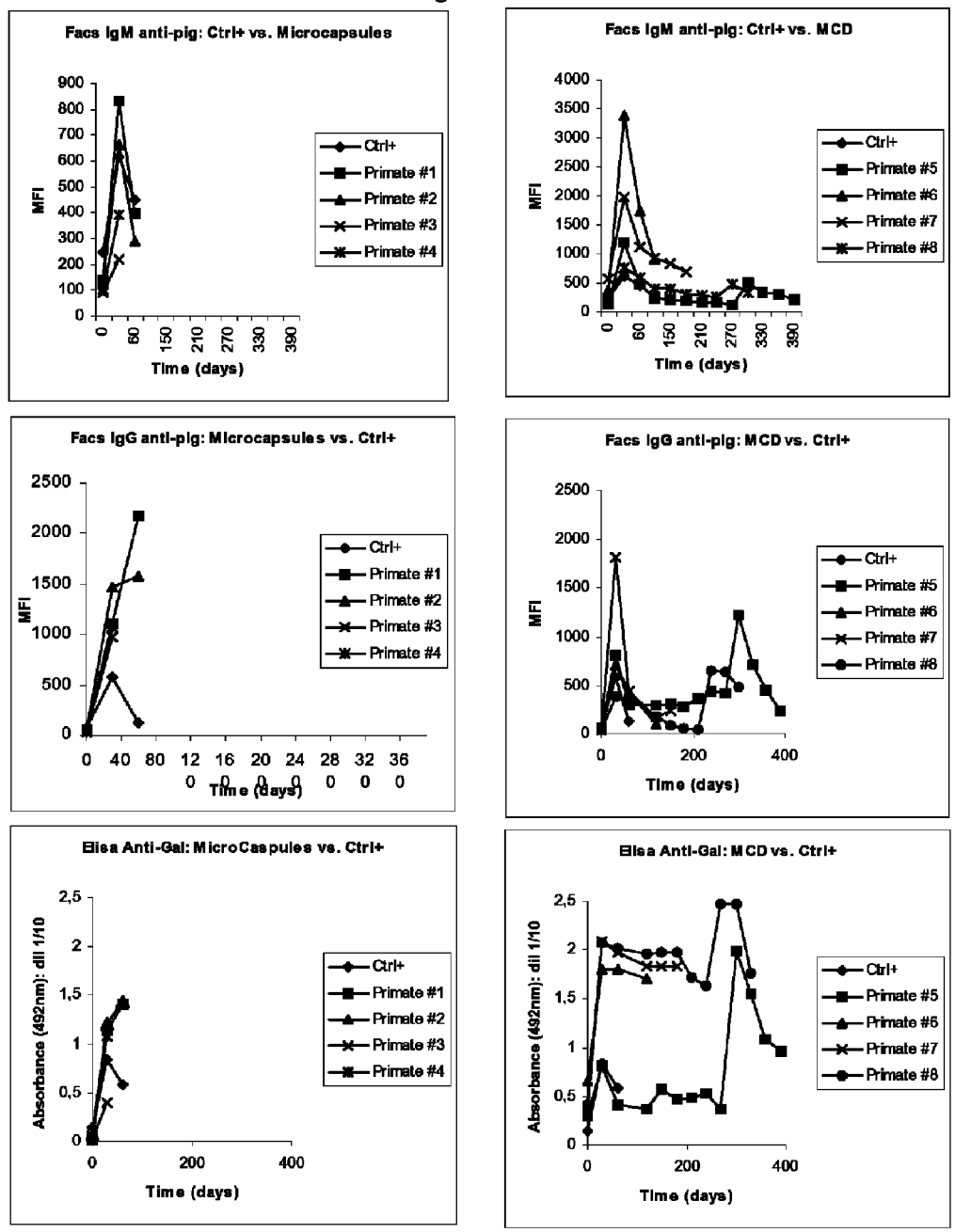
FIG. 13 depicts levels of anti-pig IgM, anti-pig IgG, and anti-gal antibodies after transplantation of the microcapsules (left) and MCD (right).

A humoral response was elicited by the transplantation of encapsulated pig islets (FIG. 13). Although an increase of anti-pig IgM and IgG antibodies were observed in the primate sera of animals transplanted with encapsulated pig islets in the MCD, the grafts function until a max of 24 weeks post-transplantation. Re-transplantation of subcutaneous matrix re-induced an humoral response whose did not induce grafts destruction.

Figure 14:
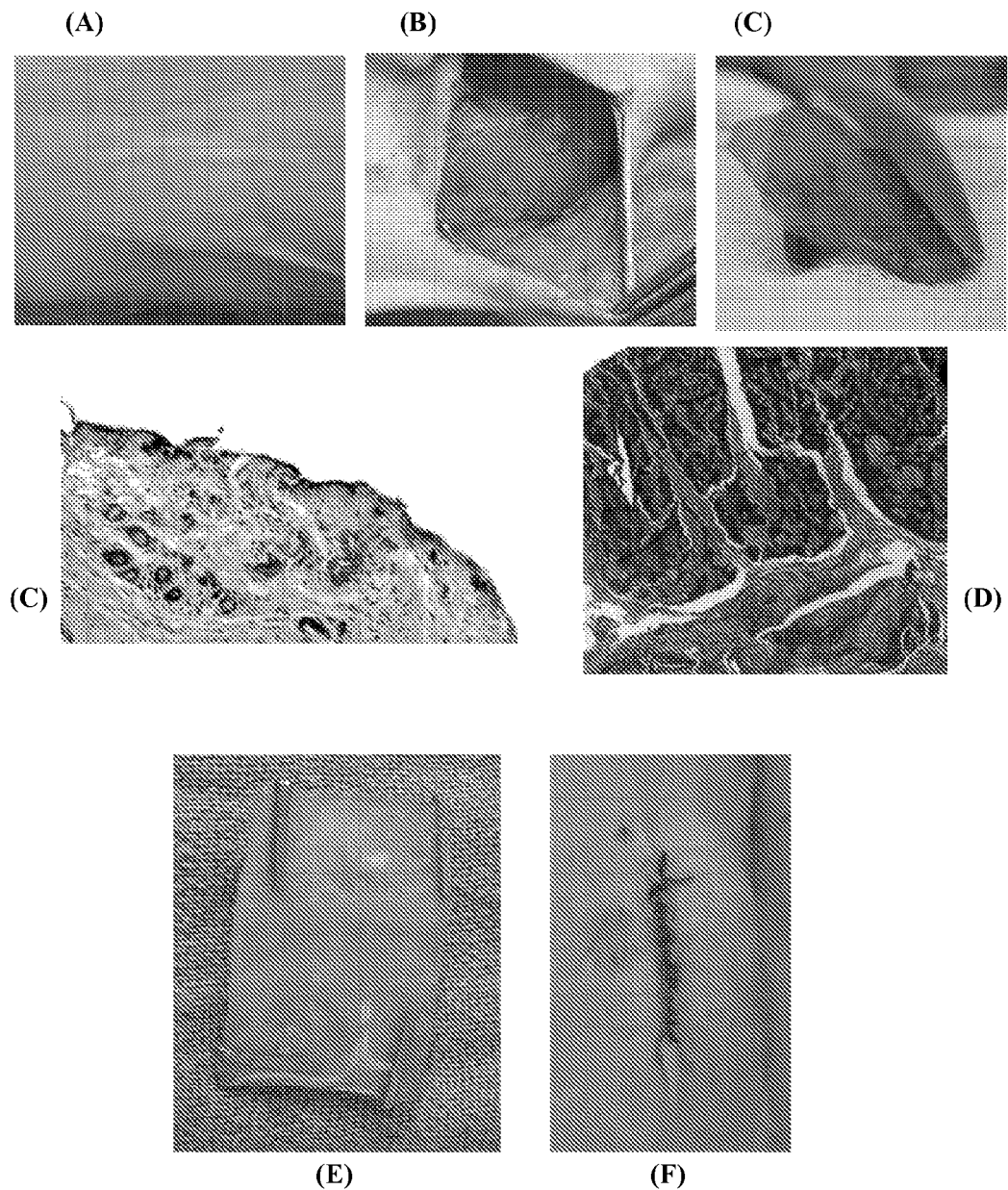
FIG. 14 depicts MCD at 34 weeks of transplantation (A) and after explantation at 34 weeks (B, C).

For Primate #8, grafts were removed at 34 weeks post-transplantation after dysfunction (FIGS. 14, A, B and C). Grafts were easily removed without any fibrosis (no lymphocyte and macrophages infiltration) and surrounding vessels (vWF staining) (FIG. 14, C), but with islets necrosis (Toluidine blue staining) (FIG. 14, D). At the same location, second grafts were placed (FIG. 14, E (second MCD); FIG. 14, F (reimplantation site).

Example 4

Revascularization of Cellular Devices after Implantation

Figure 16:
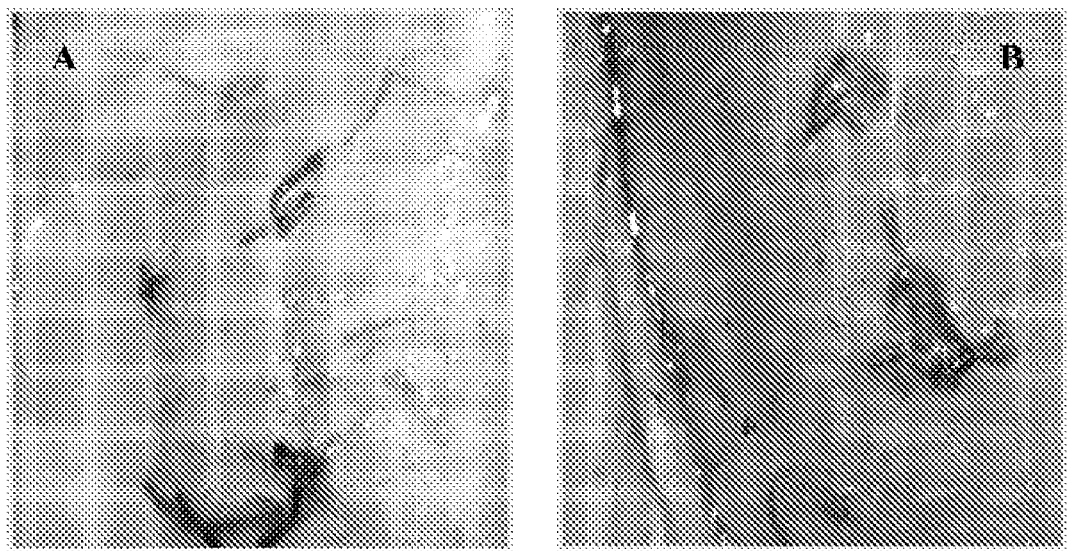
FIG. 16 depicts recolonization of fascia lata matrix at 1 month (A) and 3 months (B) post-implantation.
Figure 17:
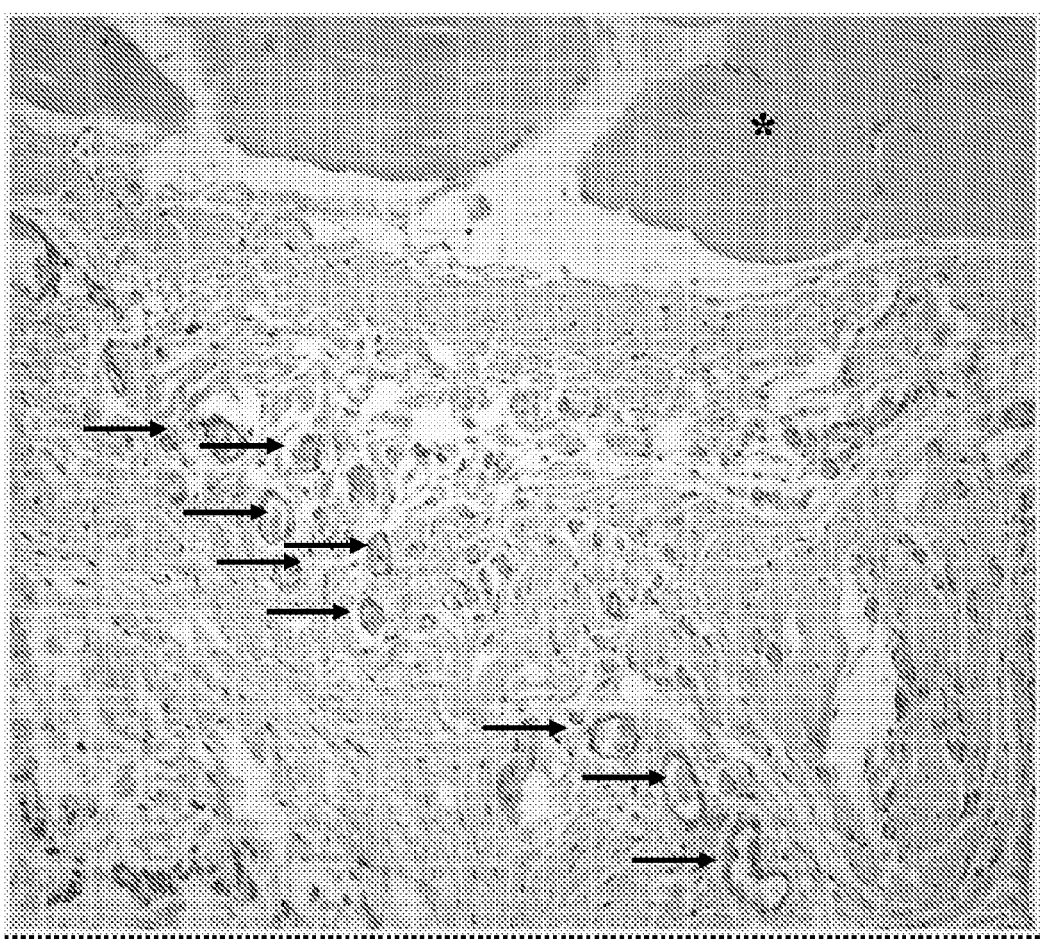
FIG. 17 depicts immunostaining for von Willebrandt factor indicating revascularization process of fascia lata. (arrow indicates vessels).

Fascia lata demonstrated its capacity to be recolonized by vascular structure and improves cell oxygenation. A cellular device (MCD) was prepared in an analogous manner to that described in Example 2, except that no islet cells were added to the device. The MCD was then implanted subcutaneously on the paravertebral muscular tissue of Wistar rats (FIG. 16). After implantation of fascia lata on muscle tissue (FIG. 16A, after one month), fascia lata is completely re-colonized by essentially vessels structure at 3 month post-implantation (FIG. 16B, after three months). Immunostaining for von Willebrandt factor indicates the revascularization of fascia lata. (arrow indicates vessels) (FIG. 17).

Example 5

Preparation and Implantation of Cellular Devices Comprising Parathyroid Cells

The encapsulation device was alternatively developed to treat patient with hypoparathyroid function associated with a very low level of blood calcium. Hypoparathyroidism results from a deficit in parathyroid hormone (PTH), which is produced by the parathyroid glands and which regulates blood calcium levels.

Figure 18:
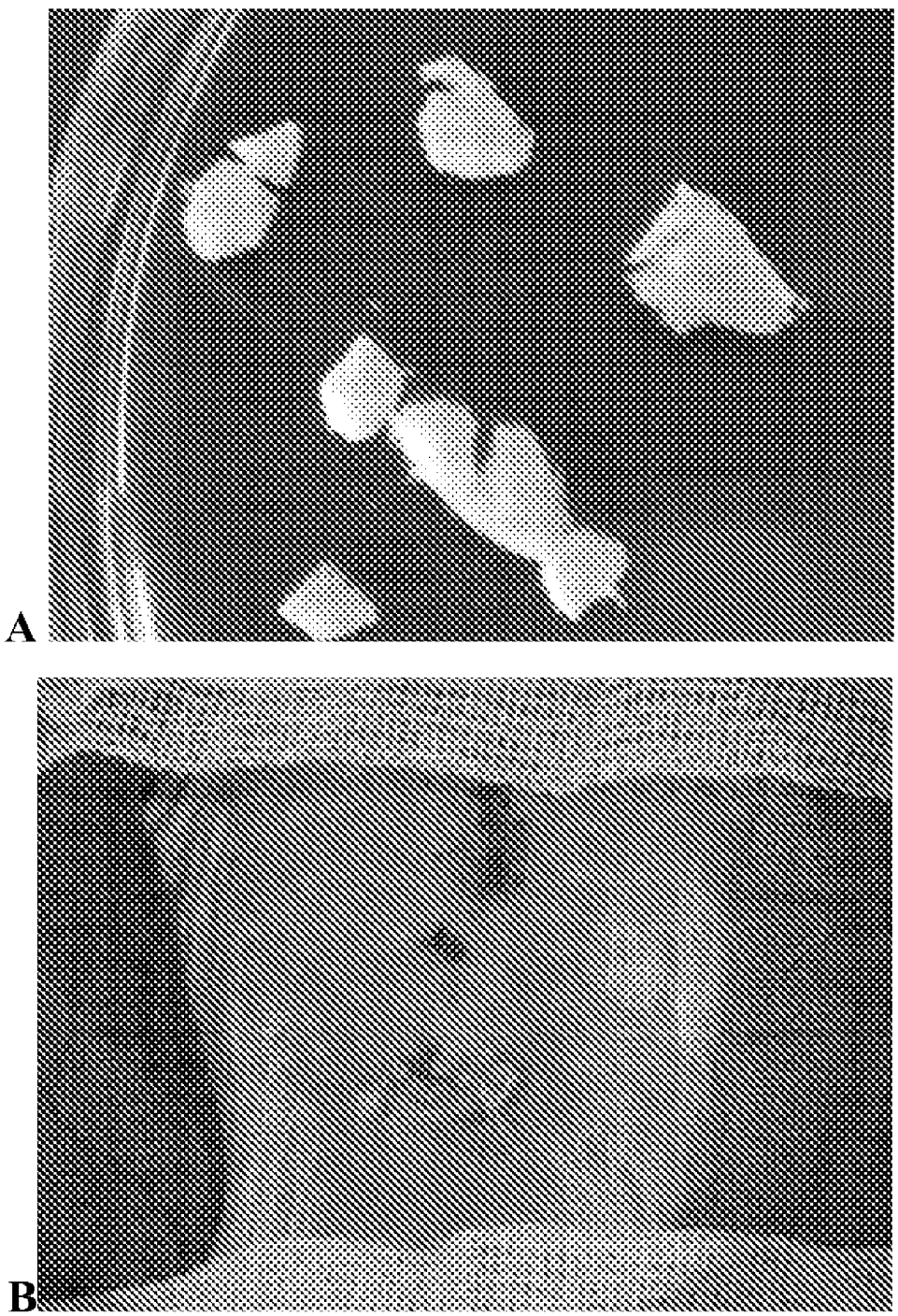
FIG. 18 depicts human parathyroid glands after mincing (A) and just after subcutaneously transplantation (for Ctrl+ animals) (B).

A cellular device was prepared according a procedure analogous to that used to prepare the MCD in Example 2, except that parathyroid cells were utilized in place of the islets. Experiments were conducted on a human to rat (Wistar rats) transplantation model. Parathyroid were removed from human patient suffering of parathyroid adenoma. Parathyroid were minced in small pieces of 3 mm×3 mm (FIG. 18A).

Figure 19:
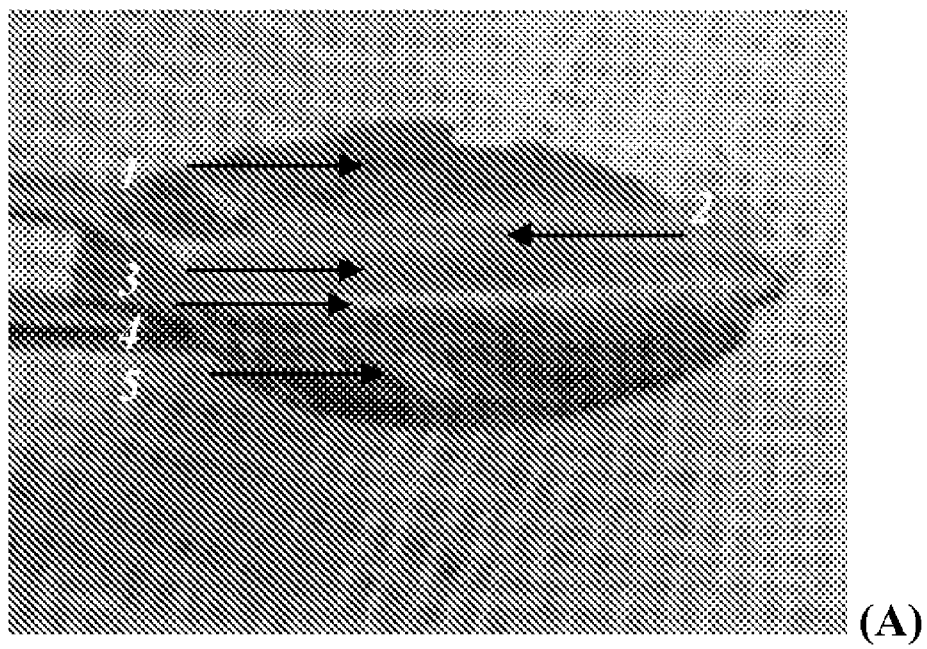
FIG. 19 depicts human parathyroid glands after encapsulation prior transplantation for the Grafts is composed by the $5^{th}$ level as 1: Alginate level; 2: Fascia Lata; 3: Parathyroid gland; 4; Polyester meshscreen; 5: Alginate.
Figure 19:
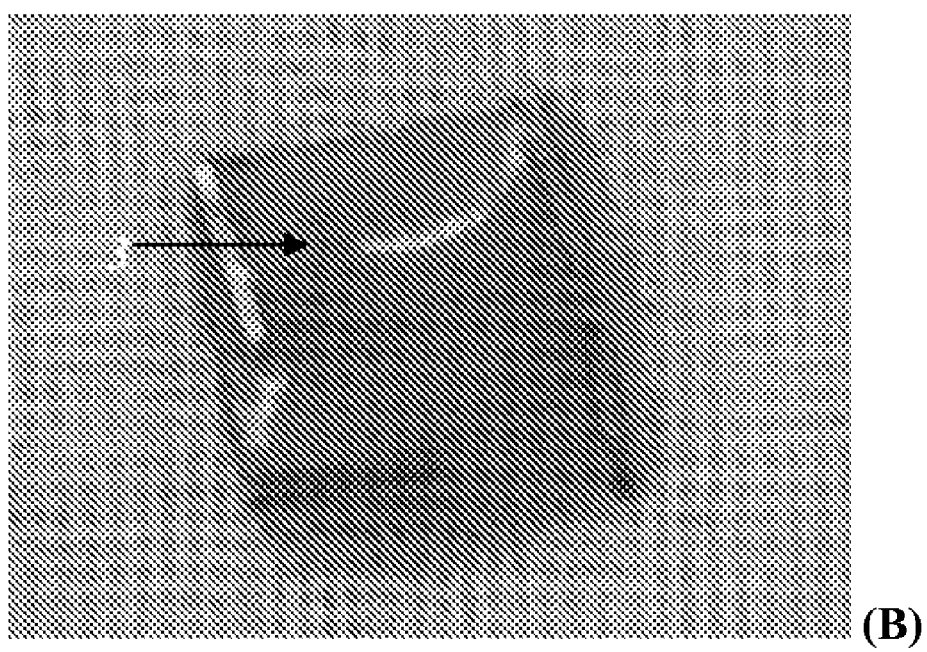

Three groups are designed:
Ctrl+ animals: non-encapsulated parathyroid glands (FIG. 18B);
Sham animals: encapsulation device without parathyroid glands;
Treated animals with encapsulated parathyroid glands (FIG. 19B).

Figure 20:
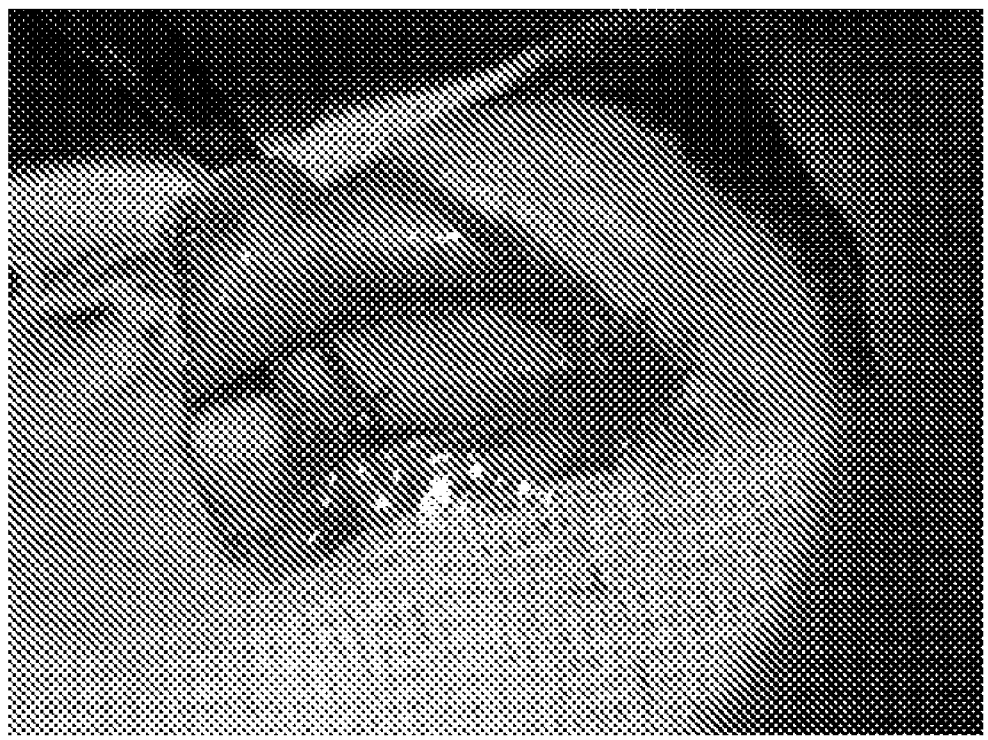
FIG. 20 depicts transplantation of encapsulation device in subcutaneous tissue of Wistar rats.
Figure 21:
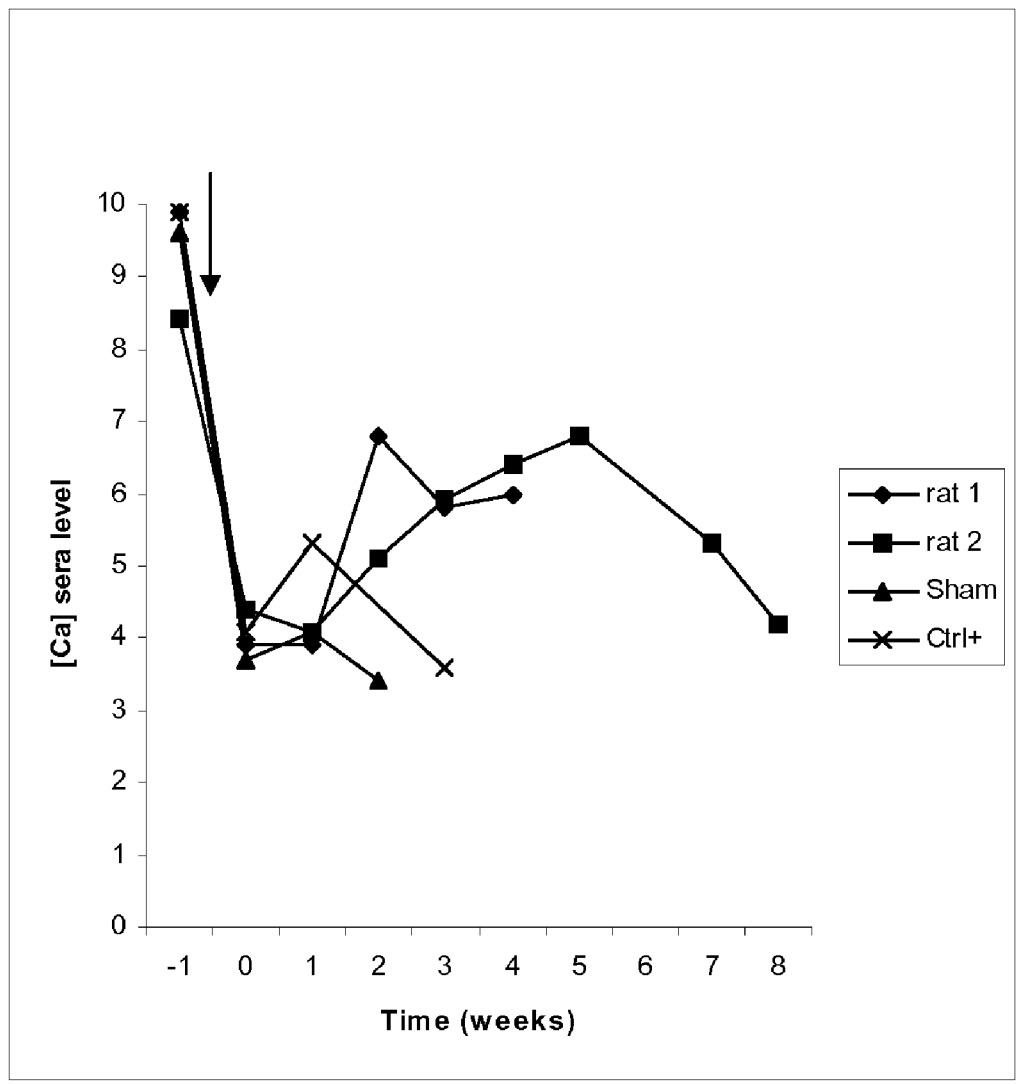
FIG. 21 depicts blood calcium course after transplantation of cellular device with or without encapsulated human parathyroid gland in subcutaneous tissue of Wistar rats (arrow indicates the corresponding time native rats parathyroid gland removal inducing a significant decrease of calcium sera level).

The devices were transplanted subcutaneously (FIG. 20) into Wistar rats. Transplantation of human encapsulated parathyroid gland demonstrated that calcium sera level can be significantly increased (rats 1 and 2) in contrast with no correction in case of the transplantation of non-encapsulated parathyroid gland (Ctrl+, graft rejection) and encapsulated empty device (Sham). (FIG. 21).

Example 6

Prophetic

Preparation and Implantation of Cellular Devices Comprising Thyroid Cells

A cellular device is prepared according a procedure analogous to that used to prepare the MCD in Example 2, except that thyroid cells are utilized in place of the islets. Experiments are conducted on a human to rat (Wistar rats) transplantation model. The devices are transplanted subcutaneously into Wistar rats.

Example 7

Prophetic

Preparation and Implantation of Cellular Devices Comprising Mesenchymal Stem Cells (MSC)

A cellular device is prepared by the method used to prepare the MCD of Example 2, except that MSC are used (10 millions of cells per 3 cm² of fascia lata). The MCD is then cultivated during one to two weeks to induce cell attachment and cell proliferation. The device is then transplanted into subcutaneous tissue of a patient.

Example 8

Prophetic

Preparation of a Cellular Device

The cellular device is prepared by the method used to prepare the MCD of Example 2, except that 5% Pronova $SLM_{20}$ (NovaMatrix, FMC Biopolymer, Norway) is used in place of the $SLM_{100}$ solutions.

Various modifications of the invention, in addition to those described herein, will be apparent to those skilled in the art from the foregoing description. Such modifications are also intended to fall within the scope of the appended claims. Each reference, including all patents, patent applications, and publications, cited in the present application is incorporated herein by reference in its entirety.

What is claimed is:

1. A cellular device comprising:
   (a) a collagen matrix having a first side and a second side;
   (b) a first cell layer absorbed onto said first side of said collagen matrix; and
   (c) a first gelled alginate layer and a second gelled alginate layer; wherein said first gelled alginate layer completely covers said first side of said collagen matrix and said first cell layer; and wherein said second gelled alginate layer completely covers said second side of said collagen matrix.

2. A cellular device according to claim 1, wherein said cellular device possess an endotoxin level of less than 100 EU/g.

3. A cellular device according to claim 1, wherein said collagen matrix comprises a material derived from fascia lata.

4. A cellular device according to claim 1, wherein said collagen matrix comprises a material derived from human fascia lata.

5. A cellular device according to claim 1, wherein said collagen matrix is a material that is chemically treated, wherein the chemical treatment comprises:
   immersing said material in a defatting solvent;
   contacting said material with a solution of base; and
   contacting said material with a solution of salt, oxidizing agent, or mixture thereof.

6. A cellular device according to claim 1, wherein said collagen matrix is sterilized by gamma radiation and treated by lyophilization.

7. A cellular device according to claim 1, wherein said first gelled alginate layer and said second gelled alginate layer each independently comprises an alginate.

8. A cellular device according to claim 1, wherein the first gelled alginate layer and second gelled alginate layer each independently comprises an alginate with a weight-average molecular weight of about 4 kD to about 300 kD.

9. A cellular device according to claim 1, wherein the first gelled alginate layer and second gelled alginate layer each independently comprises an alginate with a weight-average molecular weight of about 150 kD to about 250 kD.

10. A cellular device according to claim 1, wherein the first gelled alginate layer and second gelled alginate layer each independently comprises an alginate with a weight-average molecular weight of about 75 kD to about 150 kD.

11. A cellular device according to claim 1, wherein said first gelled alginate layer and said second gelled alginate layer comprises an alginate derived from *macrocystitis purifera*.

12. A cellular device according to claim 1, wherein said first gelled alginate layer and said second gelled alginate layer each independently comprises an RGD peptide coupled alginate.

13. A cellular device according to claim 1, wherein the first gelled alginate layer and second gelled alginate layer each independently comprises multivalent cations selected from the group consisting of calcium ions, strontium ions, barium ions, and combination thereof.

14. A cellular device according to claim 1, wherein the first gelled alginate layer and second gelled alginate layer each independently comprises calcium ions.

15. A cellular device according to claim 1, wherein said cellular device is equilibrated in a solution comprising about 1.8 mM calcium ions.

16. A cellular device according to claim 1, wherein said device is about 1 cm$^2$ to about 4 cm$^2$.

17. A cellular device according to claim 1, further comprising a structural support.

18. A cellular device according to claim 1, further comprising a structural support, wherein said structural support placed onto said second side of said collagen matrix or onto said first cell layer; wherein:
   said first gelled alginate layer or said second gelled alginate layer completely covers said structural support;
   provided that if said structural support is placed on said first cell layer, said structural support is permeable to nutrients.

19. A cellular device according to claim 18, wherein said structural support comprises a mesh.

20. A cellular device according to claim 19, wherein said structural support comprises polyester.

21. A cellular device according to claim 18, further comprising one or more clips affixing said structural support to said collagen matrix.

22. A cellular device according to claim 1, further comprising a second cell layer absorbed onto said second side of said collagen matrix, wherein said second gelled alginate layer completely covers said second cell layer.

23. A cellular device according to claim 22, further comprising a structural support placed onto said second cell layer, wherein:
said second gelled alginate layer completely covers said structural support; and
said structural support is permeable to nutrients.

24. A cellular device according to claim 1, wherein said first cell layer comprises cells are selected from the group consisting of pancreatic islet cells, mesenchymal stem cells, parathyroid cells, thyroid cells, hepatic cells, neural cells, vascular endothelial cells, thyroid cells, adrenal cells, thymic cells, or ovarian cells.

25. A cellular device according to claim 1, said first cell layer comprises pancreatic islet cells or parathyroid cells.

26. A cellular device according to claim 1, said first cell layer comprises pancreatic islet cells.

27. A cellular device according to claim 1, wherein said first cell layer comprises about 20,000 to about 40,000 pancreatic islet cells per $cm^2$.

28. A cellular device according to claim 1, wherein:
said collagen matrix comprises a material derived from human fascia lata; and
said first gelled alginate layer and second gelled alginate layer each independently comprise a RGD coupled alginate and multivalent cations selected from the group consisting of calcium ions, barium ions, strontium ions or combination thereof.

29. A cellular device according to claim 1, wherein:
said collagen matrix comprises a material derived from human fascia lata; and
said first gelled alginate layer and second gelled alginate layer each independently comprise a modified alginate and multivalent cations selected from the group consisting of calcium ions, barium ions, strontium ions or combination thereof.

30. A cellular device according to claim 29, wherein said an alginate has a weight-average molecular weight of about 50 kD to about 300 kD.

31. A cellular device according to claim 30, further comprising a structural support placed onto said first cell layer, wherein said structural support is permeable to nutrients.

32. A cellular device according to claim 31, wherein said first cell layer comprises pancreatic islet cells, mesenchymal stem cells, parathyroid cells, thyroid cells, hepatic cells, neural cells, vascular endothelial cells, thyroid cells, adrenal cells, thymic cells, or ovarian cells.

33. A cellular device according claim 31, wherein said first cell layer comprises pancreatic islet cells.

34. A cellular device according to claim 33, further comprising two or more clips affixing said collagen matrix to said structural support.

35. A cellular device according to claim 1, wherein:
said collagen matrix comprises a material derived from human fascia lata;
said first cell layer comprises about 20,000 to about 40,000 pancreatic islet cells;
said first gelled alginate layer and second gelled alginate layer each independently comprises calcium ions and an alginate with a weight-average molecular weight of about 4 kD to about 300 kD;
said cellular device is equilibrated in a solution comprising about 1.8 mM calcium ions;
a structural support placed onto said first cell layer; and
two or more clips affixing said structural support to said collagen matrix;
wherein:
said first gelled alginate layer completely covers said structural support and is permeable to nutrients; and
said structural support comprises a polyester mesh.

36. A kit for implanting one or more devices in a patient in need thereof, comprising one or more cellular devices according to claim 1.

* * * * *

SEQUENCE LISTING

<160> NUMBER OF SEQ ID NOS: 22

<210> SEQ ID NO 1
<211> LENGTH: 5
<212> TYPE: PRT
<213> ORGANISM: Artificial Sequence
<220> FEATURE:
<223> OTHER INFORMATION: Cell Adhesion Peptide 1

<400> SEQUENCE: 1

Tyr Ile Gly Ser Arg
1               5

```
<210> SEQ ID NO 2
<211> LENGTH: 5
<212> TYPE: PRT
<213> ORGANISM: Artificial Sequence
<220> FEATURE:
<223> OTHER INFORMATION: Cell Adhesion Peptide 2

<400> SEQUENCE: 2

Ile Lys Val Ala Val
1               5

<210> SEQ ID NO 3
<211> LENGTH: 4
<212> TYPE: PRT
<213> ORGANISM: Artificial Sequence
<220> FEATURE:
<223> OTHER INFORMATION: Cell Adhesion Peptide 3

<400> SEQUENCE: 3

Arg Glu Asp Val
1

<210> SEQ ID NO 4
<211> LENGTH: 4
<212> TYPE: PRT
<213> ORGANISM: Artificial Sequence
<220> FEATURE:
<223> OTHER INFORMATION: Cell Adhesion Peptide 4

<400> SEQUENCE: 4

Asp Gly Glu Ala
1

<210> SEQ ID NO 5
<211> LENGTH: 6
<212> TYPE: PRT
<213> ORGANISM: Artificial Sequence
<220> FEATURE:
<223> OTHER INFORMATION: Cell Adhesion Peptide 5

<400> SEQUENCE: 5

Val Gly Val Ala Pro Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Cell Adhesion Peptide 6

<400> SEQUENCE: 6

Gly Arg Gly Asp Ser
1               5

<210> SEQ ID NO 7
<211> LENGTH: 4
<212> TYPE: PRT
<213> ORGANISM: Artificial Sequence
<220> FEATURE:
<223> OTHER INFORMATION: Cell Adhesion Peptide 7

<400> SEQUENCE: 7

Arg Gly Asp Val
1

<210> SEQ ID NO 8
<211> LENGTH: 5
```

```
<212> TYPE: PRT
<213> ORGANISM: Artificial Sequence
<220> FEATURE:
<223> OTHER INFORMATION: Cell Adhesion Peptide 8

<400> SEQUENCE: 8

Pro Asp Ser Gly Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Cell Adhesion Peptide 9

<400> SEQUENCE: 9

Arg Tyr Val Val Leu Pro Arg
1               5

<210> SEQ ID NO 10
<211> LENGTH: 6
<212> TYPE: PRT
<213> ORGANISM: Artificial Sequence
<220> FEATURE:
<223> OTHER INFORMATION: Cell Adhesion Peptide 10

<400> SEQUENCE: 10

Leu Gly Thr Ile Pro Gly
1               5

<210> SEQ ID NO 11
<211> LENGTH: 4
<212> TYPE: PRT
<213> ORGANISM: Artificial Sequence
<220> FEATURE:
<223> OTHER INFORMATION: Cell Adhesion Peptide 11

<400> SEQUENCE: 11

Arg Gly Asp Ser
1

<210> SEQ ID NO 12
<211> LENGTH: 4
<212> TYPE: PRT
<213> ORGANISM: Artificial Sequence
<220> FEATURE:
<223> OTHER INFORMATION: Cell Adhesion Peptide 12

<400> SEQUENCE: 12

Arg Gly Asp Phe
1

<210> SEQ ID NO 13
<211> LENGTH: 12
<212> TYPE: PRT
<213> ORGANISM: Artificial Sequence
<220> FEATURE:
<223> OTHER INFORMATION: Cell Adhesion Peptide 13

<400> SEQUENCE: 13

His His Leu Gly Gly Ala Leu Gln Ala Gly Asp Val
1               5                   10

<210> SEQ ID NO 14
<211> LENGTH: 4
<212> TYPE: PRT
<213> ORGANISM: Artificial Sequence
```

```
<220> FEATURE:
<223> OTHER INFORMATION: Cell Adhesion Peptide 14

<400> SEQUENCE: 14

Val Thr Cys Gly
1

<210> SEQ ID NO 15
<211> LENGTH: 4
<212> TYPE: PRT
<213> ORGANISM: Artificial Sequence
<220> FEATURE:
<223> OTHER INFORMATION: Cell Adhesion Peptide 15

<400> SEQUENCE: 15

Ser Asp Gly Asp
1

<210> SEQ ID NO 16
<211> LENGTH: 6
<212> TYPE: PRT
<213> ORGANISM: Artificial Sequence
<220> FEATURE:
<223> OTHER INFORMATION: Cell Adhesion Peptide 16

<400> SEQUENCE: 16

Gly Arg Glu Asp Val Tyr
1               5

<210> SEQ ID NO 17
<211> LENGTH: 5
<212> TYPE: PRT
<213> ORGANISM: Artificial Sequence
<220> FEATURE:
<223> OTHER INFORMATION: Cell Adhesion Peptide 17

<400> SEQUENCE: 17

Gly Arg Gly Asp Tyr
1               5

<210> SEQ ID NO 18
<211> LENGTH: 6
<212> TYPE: PRT
<213> ORGANISM: Artificial Sequence
<220> FEATURE:
<223> OTHER INFORMATION: Cell Adhesion Peptide 18

<400> SEQUENCE: 18

Gly Arg Gly Asp Ser Pro
1               5

<210> SEQ ID NO 19
<211> LENGTH: 4
<212> TYPE: PRT
<213> ORGANISM: Artificial Sequence
<220> FEATURE:
<223> OTHER INFORMATION: Cell Adhesion Peptide 19

<400> SEQUENCE: 19

Val Ala Pro Gly
1

<210> SEQ ID NO 20
<211> LENGTH: 9
<212> TYPE: PRT
<213> ORGANISM: Artificial Sequence
<220> FEATURE:
<223> OTHER INFORMATION: Cell Adhesion Peptide 20
```

```
-continued

<400> SEQUENCE: 20

Gly Gly Gly Gly Arg Gly Asp Ser Pro
1               5

<210> SEQ ID NO 21
<211> LENGTH: 8
<212> TYPE: PRT
<213> ORGANISM: Artificial Sequence
<220> FEATURE:
<223> OTHER INFORMATION: Cell Adhesion Peptide 21

<400> SEQUENCE: 21

Gly Gly Gly Gly Arg Gly Asp Tyr
1               5

<210> SEQ ID NO 22
<211> LENGTH: 6
<212> TYPE: PRT
<213> ORGANISM: Artificial Sequence
<220> FEATURE:
<223> OTHER INFORMATION: Cell Adhesion Peptide 22

<400> SEQUENCE: 22

Phe Thr Leu Cys Phe Asp
1               5
```